(12) United States Patent
Kampe et al.

(10) Patent No.: US 8,927,745 B2
(45) Date of Patent: Jan. 6, 2015

(54) PROCESS FOR PRODUCING PROPYLENE OXIDE

(75) Inventors: Philip Kampe, Lorsch (DE); Peter Resch, Hettenleidelheim (DE); Soo Yin Chin, Mannheim (DE); Peter Bassler, Viernheim (DE); Ulrich Mueller, Neustadt (DE); Goetz-Peter Schindler, Ludwigshafen (DE); Hans-Georg Goebbel, Kallstadt (DE); Joaquim Henrique Teles, Otterstadt (DE); Kai Gumlich, Mannheim (DE); Thomas Grassler, Limburgerhof (DE); Christian Bartosch, Mannheim (DE); Richard Jacubinas, Bloomfield, NJ (US); Meinolf Weidenbach, Stade (DE)

(73) Assignees: BASF SE, Ludwigshafen (DE); The Dow Chemical Company, Midland, MI (US)

( * ) Notice: Subject to any disclaimer, the term of this patent is extended or adjusted under 35 U.S.C. 154(b) by 170 days.

(21) Appl. No.: 13/319,803

(22) PCT Filed: May 5, 2010

(86) PCT No.: PCT/EP2010/056097
§ 371 (c)(1),
(2), (4) Date: Nov. 10, 2011

(87) PCT Pub. No.: WO2010/130610
PCT Pub. Date: Nov. 18, 2010

(65) Prior Publication Data
US 2012/0065413 A1 Mar. 15, 2012

Related U.S. Application Data

(60) Provisional application No. 61/177,415, filed on May 12, 2009.

(51) Int. Cl.
*C07D 301/12* (2006.01)

(52) U.S. Cl.
CPC ................................. *C07D 301/12* (2013.01)

USPC .......................................................... 549/531

(58) Field of Classification Search
USPC .......................................................... 549/531
See application file for complete search history.

(56) References Cited

U.S. PATENT DOCUMENTS

| | | | |
|---|---|---|---|
| 4,869,883 A | 9/1989 | Thorogood et al. | |
| 5,194,675 A | 3/1993 | Joerg et al. | |

(Continued)

FOREIGN PATENT DOCUMENTS

| | | |
|---|---|---|
| DE | 1 929 977 | 12/1969 |
| DE | 32 28 023 | 2/1984 |

(Continued)

OTHER PUBLICATIONS

U.S. Appl. No. 13/381,116, filed Dec. 28, 2011, Kunst, et al.

(Continued)

*Primary Examiner* — T. Victor Oh
(74) *Attorney, Agent, or Firm* — Oblon, Spivak, McClelland, Maier & Neustadt, L.L.P.

(57) ABSTRACT

A process for producing propylene oxide comprising reacting propene with hydrogen peroxide in the presence of a catalyst to give a mixture (G1) comprising propylene oxide, unreacted propene, and oxygen; separating propylene oxide from mixture (G1) to give a mixture (GII) comprising propene and oxygen; and adding hydrogen to mixture (GII) and reducing the oxygen comprised in mixture (GII) at least partially by reaction with hydrogen in the presence of a catalyst comprising copper in elemental and/or oxidic form on a support, wherein copper is present on the support in an amount of 30 to 80 wt.-% based on the whole catalyst and calculated as CuO.

20 Claims, 8 Drawing Sheets

(56) References Cited

U.S. PATENT DOCUMENTS

Figure 1:
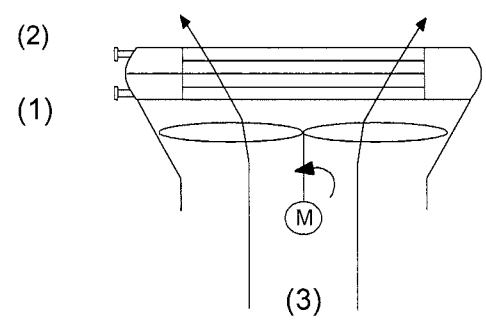

| | | |
|---|---|---|
| 5,397,475 A | 3/1995 | Millar et al. |
| 5,446,232 A | 8/1995 | Chen et al. |
| 5,932,187 A | 8/1999 | Ledon et al. |
| 6,069,288 A | 5/2000 | Ou et al. |
| 6,204,218 B1 | 3/2001 | Flick et al. |
| 6,380,119 B1 | 4/2002 | Grosch et al. |
| 2005/0281725 A1 | 12/2005 | Hague et al. |
| 2007/0004926 A1 | 1/2007 | Schindler et al. |
| 2008/0167484 A1 | 7/2008 | Schindler et al. |
| 2010/0000911 A1 | 1/2010 | Rudolf et al. |

FOREIGN PATENT DOCUMENTS

| | | |
|---|---|---|
| DE | 42 22 109 | 1/1994 |
| DE | 202 19 277 | 3/2003 |
| DE | 202 19 278 | 3/2003 |
| DE | 202 19 279 | 3/2003 |
| DE | 101 55 470 | 5/2003 |
| EP | 0 200 260 | 12/1986 |
| EP | 0 311 983 | 4/1989 |
| EP | 0 405 976 | 1/1991 |
| EP | 0 427 062 | 5/1991 |
| EP | 0 719 768 | 7/1996 |
| RU | 2126799 C1 | 2/1999 |
| WO | 98 55228 | 12/1998 |
| WO | 01 51475 | 7/2001 |
| WO | 2004 033598 | 4/2004 |
| WO | 2007 000396 | 1/2007 |
| WO | 2008 023051 | 2/2008 |

OTHER PUBLICATIONS

Dehmelt. K., "Reinigung eines Zaehlgases mit $CF_4$ fuer das aeussere Spurkammersystem von HERA-B bei hoher Strahlenlast," University of Hamburg, Department of Physics, Total 82 Pages (Oct. 1999)
Meier, W.M., et al., "Atlas of Zeolite Structure Types," Elsevier, 5$^{th}$ edition, Total 7 Pages, (2001).
Ullmann's Encyclopedia of Industrial Chemistry, "Antidiabetic Drugs to Benzoquinone and Naphthoquinone Dyes," 5$^{th}$ edition vol. A3, pp. 447-457, (1989).
International Search Report Issued Jul. 26, 2010 in PCT/EP10/56097 Filed May 5, 2010.

(2)
(1)

(3)

PROCESS FOR PRODUCING PROPYLENE OXIDE

This application is a 371 of PCT/EP2010/056097 filed May 5, 2010, and claims benefit of U.S. provisional application Ser. No. 61/177,415, filed May 12, 2009.

FIELD OF THE INVENTION

The present invention relates to a process for producing propylene oxide by epoxidation of propene with hydrogen peroxide in the presence of a catalyst, wherein a mixture (GII) obtained in the process which comprises propene and oxygen is subjected to a reduction reaction, in order to reduce oxygen by addition of and reaction with hydrogen to mixture (GII) in the presence of a catalyst comprising copper in elemental and/or oxidic form on a support, wherein copper is present on the support in an amount of 30 to 80 wt.-% based on the weight of the whole catalyst and calculated as CuO.

BACKGROUND OF THE INVENTION

Processes for reducing the concentration of oxygen in gas mixtures comprising, for example, oxygen, olefinic compounds and other carbon-comprising compounds such as hydrocarbons are already known from the prior art.

DE 101 55 470 A1 describes a method for the synthesis of propylene oxide by epoxidation of propene with recovery of unreacted propene, in which propene is recovered from at least a portion of an off-stream of the propylene oxide synthesis by (i) addition of nitrogen to the off-gas stream, (ii) compression and (iii) condensation of the resulting stream, (iv) subjecting the stream to gas permeation and (v) separation. During condensation, a gas stream comprising propene, nitrogen and oxygen is separated from a liquid stream and fed to gas permeation. Addition of nitrogen is conducted so as to obtain a stream resulting from retentate of the gas permeation which has a low content of oxygen. Thus, formation of an ignitable mixture is avoided.

EP 0 719 768 A1 describes a process for recovering an olefin and oxygen which are comprised in an off-gas stream obtained from catalytic reaction of the olefin with hydrogen peroxide. In this separation process, the off-gas stream is contacted with an absorption agent such as isopropanol. In order to avoid ignitiable gas mixture, an inert gas like methane has to be added.

In his diploma thesis, K. Dehmel, University of Hamburg, Department of Physics, October 1999, discloses that a gas mixture of argon, $CF_4$ and carbon dioxide can be freed from oxygen by catalytical hydrogenation of oxygen using hydrogen gas in the presence of a catalyst, namely copper oxide on a magnesium silicate-support. This document does not disclose gas mixtures comprising olefins and oxygen, from which oxygen shall be removed.

U.S. Pat. No. 6,204,218 B1 discloses a catalyst and a process for purifying streams of materials. The catalyst used comprises in its active composition from 0.05 to 1.0% by weight of at least one metal or compound of a metal of the $10^{th}$ group of the Periodic Table of the Elements and from 0.05 to 1.0% by weight of at least one metal or compound of the metal of the $11^{th}$ group of the Periodic Table of the Elements, with the weight ratio of the metal of the $11^{th}$ group to the metal of the $10^{th}$ group being from 0.95 to 1.05 and, as support, an $SiO_2$-containing catalyst support. This catalyst can be used in processes for removing alkynes, dienes and/or monounsaturated hydrocarbons or oxygen from streams of materials.

U.S. Pat. No. 6,069,288 discloses a process for selectively separating hydrogen, or both hydrogen and carbon monoxide from olefinic hydrocarbons. This separation is achieved by contacting the mixture with oxygen over a catalyst at conditions sufficient to oxidize the hydrogen to form water while suppressing reaction of the reactive, unsaturated hydrocarbons. The catalyst contains at least one metal or metal oxide from groups IB, IIB, IIIB, IVB, VB, VIB, VIIB, and VIII of the Periodic Table of the Elements. In order to oxidize hydrogen present in the mixture which is to be treated, oxygen is added to this mixture in an amount being less than the stoichiometric amount required to react with the hydrogen, and optionally any carbon monoxide. In a second stage, the remaining carbon monoxide is reacted with water in a water gas-shift reaction to give carbon dioxide and hydrogen, and any remaining hydrogen is reacted with the small portion of the active unsaturated hydrocarbon present.

U.S. Pat. No. 4,869,883 discloses an inert gas purifier for bulk nitrogen without the use of hydrogen or other reducing gases. A three stage process is disclosed using copper, copper oxide and a molecular sieve adsorbent for the sequential removal of oxygen, hydrogen, carbon monoxide, carbon dioxide and water from an inert gas feed. The oxygen being present in the bulk inert gas stream is reacted with the carbon monoxide and hydrogen present in the bulk inert gas stream in the presence of a reduced copper containing catalyst at a temperature from 150 to 250° C., to form carbon dioxide and water. Unreacted carbon monoxide and hydrogen from this step are reacted with the oxygen component of a copper oxide containing catalysts at a temperature from 150 to 250° C. to form carbon dioxide, water, and reduced copper. Water and carbon dioxide are removed by adsorption on an adsorbent, preferably a molecular sieve adsorbent.

WO 2008/023051 A1 discloses a process for the elimination of oxygen, nitrogen oxides, acetylenes, and/or dienes from hydrogen-rich olefin-containing gas-mixtures. The gas-mixture further comprises hydrogen, one or more olefins, not being dienes, and optionally further components, and is brought into contact with a catalyst in a reaction zone, wherein the catalyst comprises copper(I) sulfide.

DE 19 29 977 discloses a process for the purification of olefins, comprising contacting a mixture comprising olefins, for example ethylene and propylene, in the gas phase with a catalytical mass comprising copper oxide (CuO) which can be regenerated subsequently with a gas comprising oxygen. Hydrogen is removed from said gas mixture by reaction with copper(I) oxide to obtain copper in elemental form and water. By treating copper in elemental form with oxygen gas, copper (II) oxide is formed again.

DE 32 28 023 A1 discloses a process for obtaining hydrocarbons from a gas mixture comprising 5 to 15% by volume oxygen, wherein the hydrocarbon is adsorbed at a suitable adsorbant. Prior to adsorption, the amount of oxygen can be reduced by catalytical reduction. In this reduction, a copper catalyst is used comprising copper in an amount of less than 5% by weight.

U.S. Pat. No. 5,446,232 discloses a further process for removing oxygen from hydrocarbon gases. With this method it is possible to remove oxygen from hydrogen, hydrocarbon or halogenated hydrocarbon gas containing from about 0.01 to about 10 mol-% oxygen. The oxygen removal is accomplished by contacting the gas with a hopcalite catalyst. Oxygen is removed by reaction with the hydrocarbons present in the mixture to form water and carbon dioxide. The catalyst is a mixture of CuO and $MnO_2$.

WO 2004/033598 A1 describes a process for the removal of oxygen from a gas mixture comprising oxygen, at least one olefin, hydrogen, carbon monoxide and optionally at least one alkyne wherein the ratio of oxygen:hydrogen in the gas mixture is 1 part by volume of oxygen to at least 5 parts of volume of hydrogen, i.e., the volume ratio of oxygen to hydrogen must be smaller than or equal to 0.2. Accordingly, examples 9 and 10 of WO 2004/033598 A1 disclose gas streams having a molar oxygen:hydrogen ratio of 0.0034, i.e. a molar hydrogen:oxygen ratio of 294, and examples 11 and 12 disclose gas streams having an oxygen:hydrogen ratio of 0.0052, i.e. a molar hydrogen:oxygen ratio of 192. The process comprises contacting the gas mixture with the catalyst in a reaction zone under conditions sufficient to oxidize at least a portion of the hydrogen and at least a portion of the carbon monoxide, without significant hydrogenation of the at least one olefin. The catalyst comprises at least one metal selected from the group consisting of the 10th group and the 11th group of the Periodic Table of the Elements, the metal or oxide of the metal being supported on an oxide support, provided that if the catalyst comprises at least one metal or oxide of metal from the 10th group supported on an oxide support, the catalyst also comprises tin and provided that if the catalyst comprises at least one metal or oxide of metal of the 11th group, the oxide support is a zeolite. The gas mixtures subjected to the process of WO 2004/033598 A1 are typically obtained from steam cracking of hydrocarbons, dehydrogenation of paraffinic feedstock, conversion of methanol to olefins, and autothermal cracking of hydrocarbons. The process of WO 2004/033598 A1 is particularly suitable for gas mixtures comprising from greater than 0 up to and including 60 percent by volume olefin. Advantageously, the process of WO 2004/033598 A1 enables oxygen to be removed from gas mixtures containing low levels of oxygen such as 2000 ppm or less, and especially from gas mixtures having a low concentration of oxygen and a high concentration of hydrogen such as at least 10 percent by volume of hydrogen or for example greater than 40 percent by volume of hydrogen.

In WO 01/51475 A1, a process for working up a mixture comprising an alkene and oxygen is disclosed, wherein oxygen is removed from the mixture by nondestillative methods. According to this document, oxygen can be removed by combustion or by reaction of the oxygen with at least one suitable chemical compound or by a combination of these methods. The combustion of oxygen present in the mixture is conducted in the presence of a copper-chromite catalyst. The at least one suitable compound with which oxygen is reacted is an alkane. The oxydehydrogenation reaction of an alkane and oxygen gives rise to the corresponding alkene. WO 01/51475 A1 does not disclose a process for removing oxygen from a mixture comprising propene in which hydrogen is added and oxygen and hydrogen react to give water in the presence of a catalyst.

Accordingly, the prior art describes, on the one hand, industrial processes such as dehydrogenation processes in which gas mixtures are obtained containing oxygen, hydrogen, olefin and optionally alkanes in mutual ratios which are fundamentally different from the gas mixtures obtained from epoxidation reactions such as epoxidation of propene. On the other hand, the prior art describes catalysts which do not meet the specific requirements of removing oxygen from gas mixtures obtained in epoxidation reactions such as epoxidation of propene.

Moreover, adsorption techniques described in the prior art have the major disadvantage that during adsorption of propene, the explosive range of propene/oxygen mixtures is passed due to the increasing concentration of oxygen. Consequently, in order to avoid process risks, apparatuses used for sorption techniques have to be constructed highly pressure resistant, thus causing high costs which in turn render the overall process economically undesirable. Alternatively or additionally, at least one suitable inert gas would have to be added, with additional costs for such further chemical compounds incurred. Furthermore, known methods based on reactive adsorption, especially as far as adsorption of oxygen is concerned, require the periodical regeneration of the adsorbent.

Therefore, it is an object of the present invention to provide a process for producing propylene oxide in which an effective removal of oxygen from gas mixtures directly or indirectly obtained from the epoxidation reaction of propene is achieved.

It is another object of the present invention to provide a catalyst for use in a work-up stage of a process for producing propylene oxide, in which work-up stage oxygen is effectively removed from a gas mixture.

It is still another object of the present invention to provide a work-up stage in a process for producing propylene oxide, in which work-up stage oxygen is effectively removed from a gas mixture comprising oxygen and propene wherein the disadvantages of sorption process are avoided.

It is still another object of the present invention to provide a work-up stage in a process for producing propylene oxide, in which work-up stage oxygen is effectively removed from a gas mixture comprising oxygen and propene by a specifically adapted catalyst in combination with a specifically adapted addition of hydrogen and reaction conditions which minimizes losses of propene due to hydrogenation.

SUMMARY OF THE INVENTION

The present invention provides a process for producing propylene oxide comprising (I) reacting propene with hydrogen peroxide in the presence of a catalyst to give a mixture (GI) comprising propylene oxide, unreacted propene, and oxygen;

(II) separating propylene oxide from mixture (GI) to give a mixture (GII) comprising propene and oxygen;

(III) adding hydrogen to mixture (GII) and reducing the oxygen comprised in mixture (GII) at least partially by reaction with hydrogen in the presence of a catalyst comprising copper in elemental and/or oxidic form on a support, wherein copper is present on the support in an amount of 30 to 80 wt.-% based on the whole catalyst and calculated as CuO.

The present invention, according to a preferred embodiment, also provides a process for producing propylene oxide comprising (I) reacting propene with hydrogen peroxide in the presence of a titanium silicalite catalyst, preferably a titanium silicalite-1 (TS-1) catalyst, to give a mixture (GI) comprising of from 8 to 13 wt.-% of propylene oxide, of from 2 to 7 wt.-% of unreacted propene, of from 0.01 to 1 wt.-% of propane, and of from 0.02 to 0.5 wt.-% of oxygen;

(II) separating propylene oxide from mixture (GI) to give, optionally after at least one intermediate stage, a mixture (GII) comprising of from 85 to 97.5 wt.-% of propene, of from 0.5 to 10 wt.-% of propane, and of from 2.5 to 5 wt.-% of oxygen, in each case based on the total weight of the mixture (GII);

(III) adding hydrogen to mixture (GII) and reducing the oxygen comprised in mixture (GII) at least partially by reaction with hydrogen in the presence of a catalyst comprising copper in elemental and/or oxidic form and at least one promoter supported on magnesium silicate, the catalyst having a BET surface determined according to DIN 66131 of from 20 to 300 m²/g, and a copper content of from 40 to 50 wt.-%, based on the total catalyst weight and calculated as CuO, to obtain a mixture (GIII) having an oxygen content of 150 ppm at most;

(IV) separating propene from mixture (GIII) and re-introducing the separated propene, having a preferred oxygen content of 10 ppm at most, into (I), wherein in (III), the reduction reaction is performed at a temperature of from 190 to 400° C., more preferably from 200 to 350° C. and still more preferably from 200 to 300° C., and at a pressure in the range of from 10 to 20 bar, and wherein in (III), the hydrogen is added in an amount so that the molar ratio of hydrogen to oxygen is in the range of from 0.3:1 to 3.5:1.

DETAILED DESCRIPTION OF THE INVENTION

According to the present invention, a process for producing propylene oxide is provided comprising (I) reacting propene with hydrogen peroxide in the presence of a catalyst to give a mixture (GI) comprising propylene oxide, unreacted propene, and oxygen;
(II) separating propylene oxide from mixture (GI) to give a mixture (GII) comprising propene and oxygen;
(III) adding hydrogen to mixture (GII) and reducing the oxygen comprised in mixture (GII) at least partially by reaction with hydrogen in the presence of a catalyst comprising copper in elemental and/or oxidic form on a support, wherein copper is present on the support in an amount of 30 to 80 wt.-% based on the whole catalyst and calculated as CuO.

Stage (I)

According to stage (I) of the process of the present invention, propene is reacted with hydrogen peroxide in the presence of a catalyst.

The epoxidation reaction is preferably carried out in at least one solvent. Examples of preferred solvents are, inter alia,
water,
alcohols, preferably lower alcohols, more preferably alcohols having less than 6 carbon atoms, for example methanol, ethanol, propanols, butanols and pentanols,
diols or polyols, preferably those having less than 6 carbon atoms,
ethers such as diethyl ether, tetrahydrofuran, dioxane, 1,2-diethoxymethane, 2-methoxyethanol,
esters such as methyl acetate, ethyl acetate or butyrolactone,
amides such as dimethylformamide, dimethylacetamide, N-methylpyrrolidone,
ketones such as acetone or methylethyl ketone,
nitriles such as acetonitrile, propionitrile or butyronitrile;
and mixtures of two or more of the abovementioned compounds.

If the epoxidation reaction is carried out in a solvent mixture comprising water wherein the water may be introduced as such and/or via, e.g., an aqueous hydrogen peroxide solution, preferred mixtures comprise methanol and water or ethanol and water or methanol, ethanol and water, a mixture of methanol and water being especially preferred. More preferably, the solvent mixture essentially consists of methanol and water. According to other embodiments, solvent mixtures comprise at least one nitrile and water, preferably acetonitrile and water, this mixture more preferably essentially consisting of water and acetonitrile.

The reaction according to (I) can be conducted in one, two, three or more stages. Preferably, the reaction is conducted in one, two or three stages, more preferably in one or two stages and especially preferably in two stages.

Therefore, the present invention also relates to a process as described above, wherein in (I), propene is reacted with hydrogen peroxide in the presence of a catalyst to give a mixture (GI) comprising propylene oxide, unreacted propene, and oxygen, preferably in the presence of methanol and/or a methanol/water mixture as solvent, in two reaction stages to obtain a mixture (GI) which comprises propylene oxide, unreacted propene, and oxygen, preferably additionally methanol and water.

In case acetonitrile or an acetonitrile/water mixture is used as solvent or solvent mixture, the present invention also relates to a process as described above, wherein in (I), propene is reacted with hydrogen peroxide in the presence of a catalyst to give a mixture (GI) comprising propylene oxide, unreacted propene, and oxygen, preferably in the presence of acetonitrile and/or a acetonitrile/water mixture as solvent, in one or two reaction stages to obtain a mixture (GI) which comprises propylene oxide, unreacted propene, and oxygen, preferably additionally acetonitrile and water.

According to a still further preferred embodiment, the inventive process comprises in (I) at least one such as one, two, three or more, preferably one or two, still more preferably one intermediate separation stage between two subsequent reaction stages.

Therefore, the inventive process comprises in (I) preferably at least the following sequence of stages (i) to (iii):
(i) reaction of propene with hydrogen peroxide to give a mixture comprising propylene oxide, unreacted propene, and preferably additionally methanol and water;
(ii) separation of the unreacted hydrogen peroxide from the mixture resulting from stage (i),
(iii) reaction of the hydrogen peroxide which has been separated off in stage (ii) with propene to give a mixture comprising propylene oxide.

Stage (I) of the inventive process can comprise, in addition to stages (i) and (iii), at least one further reaction stage and, in addition to stage (ii), at least one further separation stage. According to a preferred embodiment, the process stage (I) consists of these three stages (i), (ii), and (iii).

As to stages (i) and (iii), there are no specific restrictions as to how the reaction is carried out.

Accordingly, it is possible to carry out one of the reactions stages in batch mode or in semi-continuous mode or in continuous mode and independently thereof, the other reaction stage in batch mode or in semi-continuous mode or in continuous mode. According to an even more preferred embodiment, both reaction stages (i) and (iii) are carried out in continuous mode.

The epoxidation reaction in stages (i) and (iii) is carried out in the presence of at least one catalyst, preferably in the presence of at least one zeolite catalyst.

Zeolites are, as is known, crystalline aluminosilicates having ordered channel and cage structures and containing micropores which are preferably smaller than about 0.9 nm. The network of such zeolites is made up of $SiO_4$ and $AlO_4$ tetrahedra which are joined via shared oxygen bridges. An overview of the known structures may be found, for example, in W. M. Meier, D. H. Olson and Ch. Baerlocher, "Atlas of Zeolite Structure Types", Elsevier, 5th edition, Amsterdam 2001.

Zeolites in which no aluminum is present and in which part of the Si(IV) in the silicate framework is replaced by titanium as Ti(IV) are also known. Apart from silicon and titanium, such materials can further comprise additional elements such as aluminum, zirconium, tin, iron, cobalt, nickel, gallium, germanium, boron or small amounts of fluorine. In the zeolite catalysts, a portion or all of the titanium of the zeolite may have been replaced by vanadium, zirconium, chromium or niobium or a mixture of two or more thereof. The molar ratio of titanium and/or vanadium, zirconium, chromium or niobium to the sum of silicon and titanium and/or vanadium and/or zirconium and/or chromium and/or niobium is generally in the range from 0.01:1 to 0.1:1. Most preferably, zeolites are employed in which part of the Si(IV) in the silicate framework is replaced by titanium, i.e. titanium zeolites.

Titanium zeolites, in particular those having a crystal structure of the MFI type, and possible ways of preparing them are described, for example, in WO 98/55228, EP 0 311 983 A2, EP 0 405 978 A1, or in EP 0 200 260 A2.

It is known that titanium zeolites having the MFI structure can be identified via a particular X-ray diffraction pattern and also via a lattice vibration band in the infrared (IR) region at about 960 $cm^{-1}$ and thus differ from alkali metal titanates or crystalline and amorphous $TiO_2$ phases.

Specific mention may be made of titanium-, germanium-, tellurium-, vanadium-, chromium-, niobium-, zirconium-containing zeolites having a pentasil zeolite structure, in particular the types which can be assigned X-ray-crystallographically to the structures ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW, KFI, LAU, LEV, LIO, LOS, LOV, LTA, LTL, LTN, MAR, MAZ, MEI, MEL, MEP, MER, MMFI, MFS, MON, MOR, MSO, MTF, MTN, MTT, MTW, MWW, NAB, NAT, NEES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, STT, TER, THO, TON, TSC, UEI, UFI, UOZ, USI, UTL, VET, VFI, VNI, VSV, WEI, WEN, YUG and ZON, and also mixed structures of two or more of the abovementioned structures. Furthermore, titanium-containing zeolites having the ITQ-4, SSZ-24, TTM-1, UTD-1, CIT-1 or CIT-5 structure are also conceivable for use in the process of the invention. Further titanium-containing zeolites which may be mentioned are those having the ZSM-48 or ZSM-12 structure.

For the purposes of the present invention, preference is given to using Ti zeolites having an MFI structure, an MEL structure, an MFI/MEL mixed structure or an MWW structure. Further preference is given specifically to the Ti-containing zeolite catalysts which are generally referred to as "TS-1", "TS-2", TS-3", and also Ti zeolites having a framework structure isomorphous with beta-zeolite. Very particular preference is given to using zeolite catalysts of the TS-1 or TS-2 structure and the Ti-MWW structure, even more preferably of the TS-1 structure.

The catalysts, especially preferably the titanium zeolite catalysts and still more preferably the titanium zeolite catalysts having TS-1 or Ti-MWW structure, can be employed as powder, as granules, as microspheres, as shaped bodies having, for example, the shape of pellets, cylinders, wheels, stars, spheres and so forth, or as extrudates such as extrudates having, for example, a length of from 1 to 10, more preferably of from 1 to 7 and still more preferably of from 1 to 5 mm, and a diameter of from 0.1 to 5, more preferably of from 0.2 to 4 and especially preferably of from 0.5 to 2 mm. In order to increase the bulk density of the extrudates, it is preferred to cut the mass leaving the extruder with a stream essentially consisting of an inert gas.

In the specific case where a TS-1 catalyst is employed in (I), methanol or a methanol/water mixture is used as solvent, as described above.

In the specific case where a Ti-MWW catalyst is employed in (I), methanol or a methanol/water mixture can be used as solvent, as described above. More preferably, a nitrile, still more preferably acetonitrile, is used as solvent, optionally as mixture with at least one other suitable solvent such as, e.g., water.

Most preferably, a TS-1 or Ti-MWW catalyst is employed which is produced by first forming microspheres, for example microspheres formed according to EP 0 200 260 A2, and then forming said microspheres to obtain shaped bodies, preferably extrudates as described above.

For each of these forming or shaping methods according to which catalyst powder is processed to give shaped bodies such as microspheres, extrudates, granules, pellets, and the like, it is possible to use at least one additional binder and/or at least one pasting agent and/or at least one pore forming agent. Prior to using the catalyst in the epoxidation reaction of the present invention, it is possible to suitably pretreat the catalyst. In case the catalyst is used as supported catalyst, a carrier can be preferably used which is inert, i.e. which does not react with hydrogen peroxide, propene, and propylene oxide.

The reactions in stages (i) and (iii) are preferably carried out in suspension mode, fluidized-bed mode or fixed-bed mode, most preferably in fixed-bed mode.

In the inventive process, it is possible to use the same or different types of reactors in stages (i) and (iii). Thus, it is possible to carry out one of the reaction stages in an isothermal or adiabatic reactor and the other reaction stage, independently thereof, in an isothermal or adiabatic reactor. The term "reactor" as used in this respect comprises a single reactor, a cascade of at least two serially connected reactors, at least two reactors which are operated in parallel or a multitude of reactors wherein at least two reactors are serially coupled and wherein at least two reactors are operated in parallel. According to a preferred embodiment, stage (i) of the present invention is carried out in at least two reactors which are operated in parallel, and stage (iii) of the present invention is carried out in a single reactor.

Each of the reactors described above, especially the reactors according to the preferred embodiment, can be operated in downflow or in upflow operation mode.

In case the reactors are operated in downflow mode, it is preferred to use fixed-bed reactors which are preferably tubular, multi-tubular or multi-plate reactors, most preferably equipped with at least one cooling jacket. In this case, the epoxidation reaction is carried out at a temperature of from 30 to 80° C., and the temperature profile in the reactors is maintained at a level so that the temperature of the cooling medium in the cooling jackets is at least 40° C. and the maximum temperature in the catalyst bed is 60° C. In case of downflow operation of the reactors, it is possible to choose the reaction conditions such as temperature, pressure, feed rate and relative amounts of starting materials such that the reaction is carried out in a single phase, more preferably in a single liquid phase, or in a multiphase system comprising, for example, 2 or 3 phases. As to the downflow operation mode, it is especially preferred to conduct the epoxidation reaction in a multiphase reaction mixture comprising a liquid aqueous hydrogen peroxide rich phase containing methanol and a liquid organic olefin rich phase, preferably a propene rich phase.

Even more preferably, the epoxidation reaction is conducted in downflow and trickle-bed operation mode.

In case the reactors are operated in upflow mode, it is preferred to use fixed-bed reactors. It is still further preferred to use at least two fixed-bed reactors in stage (i) and at least one reactor in stage (iii). According to a still further embodiment, the at least two reactors used in stage (i) are serially connected or operated in parallel, more preferably operated in parallel. Generally, it is necessary to equip at least one of the reactors used in stage (i) and/or (iii) with a cooling means such as a cooling jacket in order to remove at least partially the heat resulting from reaction in the respective reactor. Especially preferably, at least two reactors are employed in stage (i) which are connected in parallel and can be operated alternately. In case the reactors are operated in upflow mode, the two or more reactors connected in parallel in stage (i) are particularly preferably tube reactors, multi-tube reactors or multi-plate reactors, more preferably multi-tube reactors and especially preferably shell-and-tube reactors comprising a multitude of tubes such as from 1 to 20 000, preferably from 10 to 10 000, more preferably from 100 to 8000, more preferably from 1000 to 7000 and particularly preferably from 3000 to 6000 tubes. To regenerate the catalyst used for the epoxidation reaction, it is possible for at least one of the reactors connected in parallel to be taken out of operation for the respective reaction stage and the catalyst present in this reactor to be regenerated, with at least one reactor always being available for reaction of the starting material or starting materials in every stage during the course of the continuous process.

As cooling medium used for cooling the reaction media in above-mentioned reactors equipped with cooling jackets, there are no specific restrictions. Especially preferred are oils, alcohols, liquid salts or water, such as river water, brackish water and/or sea water, which can in each case, for example, preferably be taken from a river and/or lake and/or sea close to the chemical plant in which the reactor of the invention and the process of the invention are used and, after any necessary suitable removal of suspended material by filtration and/or sedimentation, be used directly without further treatment for cooling the reactors. Secondary cooling water which is preferably conveyed around a closed circuit is particularly useful for cooling purposes. This secondary cooling water is generally essentially deionized or demineralised water to which at least one antifouling agent has preferably been added. More preferably, this secondary cooling water circulates between the reactor of the invention and, for example, a cooling tower. Preference is likewise given to the secondary cooling water being, for example, countercooled in at least one countercurrent heat exchanger by, for example, river water, brackish water and/or sea water.

In stage (iii), particular preference is given to using a shaft reactor, more preferably a continuously operated shaft reactor and particularly preferably a continuously operated, adiabatic shaft reactor. According to the present invention, it is also possible to use two or more of these reactors such as two, three or four of these reactors which are serially coupled or coupled in parallel, more preferably in parallel.

Therefore, the present invention also relates to a process as described above wherein in stage (i), at least two shell-and-tube reactors each having of from 1 to 20 000 internal tubes and being continuously operated in upflow mode, said reactors being operated in parallel, are employed, and wherein in stage (iii), one adiabatic shaft reactor or two adiabatic shaft reactors being continuously operated in upflow mode, are employed. Still more preferably, the reaction in at least one of these reactors, more preferably in the at least two reactors of stage (i) and still more preferably in all reactors used in states (i) and (iii) is conducted such that in the respective reactor, a single liquid phase is present. Even more preferably, in each of the reactors used in stages (i) and (iii), the catalyst used for the epoxidation reaction is employed as fixed-bed reactor wherein the catalyst is a titanium zeolite catalyst, more preferably a TS-1 or Ti-MWW catalyst and even more preferably a TS-1 catalyst.

Depending on the specific characteristics of the catalyst which is used as fixed-bed catalyst, it may be necessary to use at least one additional inert compound in order to keep the catalyst, for example the catalyst in the form of shaped bodies such as extrudates or the like, in fixed-bed state. Thus, at least one layer of shaped bodies consisting or essentially consisting of the at least one inert compound can be arranged below or above or below and above a catalyst layer such forming, for example, a sandwich structure. This concept can also be applied to horizontally arranged reactors. In this context, the term "inert compound" relates to a compound which does not participate in the reaction or reactions carried out in the reactor in which the inert compound is employed. As to the present epoxidation reaction, preferred inert compounds are, for example, steatite, high-fired alpha-alumina, carbides, silicides, nitrides, oxides, phosphates, ceramics, non-acidic glasses, suitable metals such as steels of types 1.4541 or 1.4571. As the geometry of the shaped bodies, there are no specific restrictions as long as the catalyst is kept in fixed-bed state. Shaped bodies such as pellets, spheres, cylinders and the like can be employed. Preferred diameters are from 2 to 35 mm, more preferably from 3 to 30 mm and more preferably from 4 to 10 mm.

The hydrogen peroxide is used in the process according to the invention in the form of an aqueous solution with a hydrogen peroxide content of generally of from 1 to 90 wt.-%, preferably of from 10 to 70 wt.-%., more preferably from 10 to 60 wt.-%. A solution having of from 20 to less than 50 wt.-% of hydrogen peroxide is particularly preferred.

According to another embodiment of the present invention, a crude aqueous hydrogen peroxide solution can be employed. As crude aqueous hydrogen peroxide solution, a solution can be used which is obtained by extraction of a mixture with essentially pure water wherein the mixture results from a process known as anthrachinone process (see, e.g., Ullmann's Encyclopedia of Industrial Chemistry, $5^{th}$ edition, volume 3 (1989) pages 447-457). In this process, the hydrogen peroxide formed is generally separated by extraction from the working solution. This extraction can be performed with essentially pure water, and the crude aqueous hydrogen peroxide is obtained. According to one embodiment of the present invention, this crude solution can be employed without further purification.

To prepare the hydrogen peroxide which is preferably used, it is possible to employ, for example, the anthraquinone process by means of which virtually the entire world production of hydrogen peroxide is produced. An overview of the anthraquinone process is given in "Ullmann's Encyclopedia of Industrial Chemistry", $5^{th}$ edition, volume 3 (1989), pages 447 to 457.

It is likewise conceivable to obtain hydrogen peroxide by converting sulfuric acid into peroxodisulfuric acid by anodic oxidation with simultaneous evolution of hydrogen at the cathode. Hydrolysis of the peroxodisulfuric acid then leads via peroxomonosulfuric acid to hydrogen peroxide and sulfuric acid which is thus obtained back.

Of course, the preparation of hydrogen peroxide from the elements is also possible.

Before hydrogen peroxide is used in the process of the invention, it is possible to free, for example, a commercially available hydrogen peroxide solution of undesirable ions. Conceivable methods are, inter alia, those described, for example, in U.S. Pat. No. 5,932,187, DE 42 22 109 A1 or U.S. Pat. No. 5,397,475. It is likewise possible to remove at least one salt present in the hydrogen peroxide solution from the hydrogen peroxide solution by means of ion exchange in an apparatus which contains at least one non-acidic ion exchanger bed having a flow cross-sectional area F and a height H which are such that the height H of the ion exchanger bed is less than or equal to $2.5 \cdot F^{1/2}$, in particular less than or equal to $1.5 \cdot F^{1/2}$. For the purposes of the present invention, it is in principle possible to use all non-acidic ion exchanger beds comprising cation exchangers and/or anion exchangers. It is also possible for cation and anion exchangers to be used as mixed beds within one ion exchanger bed. In a preferred embodiment of the present invention, only one type of non-acidic ion exchangers is used. Further preference is given to the use of basic ion exchange, particularly preferably that of a basic anion exchanger and more particularly preferably that of a weakly basic anion exchanger.

The reaction in the reactors according to stage (i) is preferably carried out at reaction conditions such that the hydrogen peroxide conversion is at least 80%, more preferably at least 85% and still more preferably at least 90%. The pressure in the reactors is generally in the range of from 10 to 30 bar, more preferably from 15 to 25 bar. The temperature of the cooling water is in the range of preferably from 20 to 70° C., more preferably from 25 to 65° C. and particularly preferably from 30 to 60° C.

According to the preferred embodiment of the invention according to which the reactor or the reactors in stage (i) are fixed-bed reactors, the product mixture obtained therefrom essentially consists of propylene oxide, unreacted propene, methanol, water, and hydrogen peroxide, and optionally propane.

According to a preferred embodiment, the product mixture obtained from stage (i) has a methanol content in the range of from 55 to 75 wt.-%, especially preferably of from 60 to 70 wt.-%, based on the total weight of the product mixture, a water content in the range of from 5 to 25 wt.-%, especially preferably of from 10 to 20 wt.-%, based on the total weight of the product mixture, a propylene oxide content in the range of from 5 to 20 wt.-%, especially preferably of from 8 to 15 wt.-%, based on the total weight of the product mixture, and a propene content in the range of from 1 to 10 wt.-%, especially preferably of from 1 to 5 wt.-%, based on the total weight of the product mixture.

According to stage (ii), unreacted hydrogen peroxide is separated from the mixture resulting from stage (i). This separation can be conducted by essentially every suitable method. Preferably, this separation is carried out by distillation using at least one distillation column. The reaction mixture obtained from the at least one reactor, preferably from the at least two reactors used in stage (i), comprising unreacted propene, propylene oxide, methanol, water and unreacted hydrogen peroxide, is introduced in the distillation column. The distillation column is preferably operated at a top pressure of from 1 to 10 bar, more preferably of from 1 to 5 bar, more preferably of from 1 to 3 bar and still more preferably of from 1 to 2 bar such as 1, 1.1, 1.2, 1.3, 1.4, 1.5, 1.6, 1.7, 1.8, 1.9 or 2 bar. According to an especially preferred embodiment, the distillation column has from 5 to 60, preferably from 10 to 50 and especially preferably from 15 to 40 theoretical stages.

According to a still further preferred embodiment, the reaction mixture obtained from (i) is fed to the distillation column of (ii) from 2 to 30 theoretical stages below the top, preferably from 10 to 20 theoretical stages below the top of the column.

The temperature of the product mixture obtained from stage (i) is preferably in the range of from 40 to 60° C., more preferably of from 45 to 55° C. Prior to being fed to the distillation column of (ii), the product mixture is preferably heated up in at least one heat exchanger to a temperature in the range of from 50 to 80° C., more preferably of from 60 to 70° C.

Heating up the product stream obtained from stage (i) is preferably carried out using, at least partially, the bottoms stream of the distillation column of stage (ii). Thus, heat integration of the overall epoxidation process is improved. According to a preferred embodiment, of from 50 to 100%, more preferably of from 80 to 100% and especially preferably of from 90 to 100% of the bottoms stream obtained from the distillation column used in (ii) are used for heating up the product stream obtained from (i) from a temperature in the range of from 45 to 55° C. to a temperature in the range of from 65 to 70° C.

At the top of the distillation column of (ii), a stream essentially consisting of propylene oxide, methanol, oxygen and unreacted propene, is obtained. At the top of the column, a mixture is obtained having a water content of not more than 0.5 wt.-%, preferably of not more than 0.4 wt.-% and still more preferably of not more than 0.3 wt.-%, and having a hydrogen peroxide content of not more than 100 ppm, preferably of not more than 20 ppm and still more preferably of not more than 10 ppm, in each case based on the total weight of the mixture obtained at the top of the column. Preferably, this stream has an oxygen content of from 0.01 to 1 wt.-%, more preferably from 0.03 to 0.75 wt.-% and still more preferably from 0.05 to 0.5 wt.-%.

At the bottom of the distillation column, a stream essentially consisting of methanol, water and unreacted hydrogen peroxide is obtained. At the bottom of the column, a mixture is obtained having a propene content of not more than 50 ppm, preferably of not more than 10 ppm and still more preferably of not more than 5 ppm, and having a propylene oxide content of not more than 50 ppm, preferably of not more than 20 ppm and still more preferably of not more than 10 ppm, in each case based on the total weight of the mixture obtained at the bottom of the column.

Therefore, depending on the respective point of view, distillative separation according to stage (ii) can be described, for example, as separation of unreacted hydrogen peroxide or, alternatively, as separation of propylene oxide.

According to a preferred embodiment of the present invention, the evaporator of the distillation column used in stage (ii) is at least partially operated using at least partially a top stream (Td). Preferably, from 5 to 60%, more preferably from 15 to 50 and especially preferably from 20 to 40% of such top stream (Td) are used to operate the evaporator of the distillation column of stage (ii). This top stream (Td) is most preferably obtained in the inventive epoxidation process in a downstream work-up stage where methanol is separated from a mixture comprising water and at least 55 wt.-% of methanol, more preferably water and at least one compound having a boiling temperature lower than methanol and lower than water at a given pressure, such as aldehydes such as, for example, acetaldehyde and/or propionaldehyde, or other compounds such as dioxolanes, and at least 60 wt.-% of methanol, in at least one distillation stage to obtain a mixture (M1) comprising at least 85 wt.-% of methanol and up to 10 wt.-% of water, and a mixture (M2) comprising at least 90 wt.-% of water.

According to a still further preferred embodiment, the distillation column used in (ii) is configured as a dividing wall column having at least one side-offtake, preferably one side-offtake. Preferably, the dividing wall column preferably has from 20 to 60, more preferably from 30 to 50 theoretical stages.

The upper combined region of the inflow and offtake part of the dividing wall column preferably has from 5 to 50%, more preferably from 15 to 30%, of the total number of theoretical stages in the column, the enrichment section of the inflow part preferably has from 5 to 50%, more preferably from 15 to 30%, the stripping section of the inflow part preferably has from 15 to 70%, more preferably from 20 to 60%, the stripping section of the offtake part preferably has from 5 to 50%, more preferably from 15 to 30%, the enrichment section of the offtake part preferably has from 15 to 70%, more preferably from 20 to 60%, and the lower combined region of the inflow and offtake part of the column preferably has from 5 to 50%, more preferably from 15 to 30%, in each case of the total number of theoretical stages in the column.

It is likewise advantageous for the inlet via which the product mixture obtained from (i) is fed into the column and the side offtake via which a part of the methanol, preferably of from 0 to 50%, more preferably of from 1 to 40%, still more preferably of from 5 to 30% and especially preferably of from 10 to 25% of the methanol, is taken off as intermediate boiler and, still more preferably, directly fed back to stage (i), to be arranged at different heights in the column relative to the position of the theoretical stages. The inlet is preferably located at a position which is from 1 to 25, more preferably from 5 to 15 theoretical stages above or below the side offtake.

The dividing wall column used in the process of the present invention is preferably configured either as a packed column containing random packing or ordered packing or as a tray column. For example, it is possible to use sheet metal or mesh packing having a specific surface area of from 100 to 1000 m$^2$/m$^3$, preferably from about 250 to 750 m$^2$/m$^3$, as ordered packing. Such packing provides a high separation efficiency combined with a low pressure drop per theoretical stage.

In the above mentioned configuration of the column, the region of the column divided by the dividing wall, which consists of the enrichment section of the inflow part, the stripping section of the offtake part, the stripping section of the inflow part and the enrichment section of the offtake part, or parts thereof is/are provided with ordered packing or random packing. The dividing wall can be thermally insulated in these regions.

The differential pressure over the dividing wall column can be utilized as regulating parameter for the heating power. The distillation is advantageously carried out at a pressure at the top of from 1 to 10 bar, preferably from 1 to 5 bar, more preferably from 1 to 3 bar and still more preferably of from 1 to 2 bar such as 1, 1.1, 1.2, 1.3, 1.4, 1.5, 1.6, 1.7, 1.8, 1.9 or 2 bar.

The distillation is then preferably carried out in a temperature range of from 65 to 100° C., more preferably of from 70 to 85° C. The distillation temperature is measured at the bottom of the tower.

In case such a divided wall column is used, at the top of the distillation column of (ii), a stream essentially consisting of propylene oxide, methanol, oxygen and unreacted propene, is obtained. At the top of the column, a mixture is obtained having a water content of not more than 500 ppm, preferably of not more than 400 ppm, and still more preferably of not more than 300 ppm, and having a hydrogen peroxide content of not more than 50 ppm, preferably of not more than 20 ppm and still more preferably of not more than 10 ppm, in each case based on the total weight of the mixture obtained at the top of the column. Furthermore, the top stream obtained has a propene content of from 15 to 35 wt.-%, preferably of from 20 to 30 wt.-% and still more preferably of from 20 to 25 wt.-%, a propylene oxide content of from 50 to 80 wt.-%, preferably of from 55 to 75 wt.-% and especially preferably of from 60 to 70 wt.-%, and a methanol content of from 5 to 20 wt.-%, more preferably of from 7.5 to 17.5 wt.-% and especially preferably of from 10 to 15 wt.-%, in each case based on the total weight of the top stream. Preferably, this top stream has an oxygen content of from 0.01 to 1 wt.-%, more preferably from 0.03 to 0.75 wt.-% and still more preferably from 0.05 to 0.5 wt.-%.

At the side-offtake of the distillation column, a stream essentially consisting of methanol and water is obtained. At the side-offtake of the column, a mixture is obtained having a methanol content of at least 95 wt.-%, preferably at least 96 wt.-% and still more preferably at least 97 wt.-%, and having a water content of not more than 5 wt.-%, preferably of not more than 3.5 wt.-% and still more preferably of not more than 2 wt.-%, in each case based on the total weight of the mixture obtained at the side-offtake of the column.

At the bottom of the distillation column, a stream essentially consisting of methanol, water and unreacted hydrogen peroxide is obtained. At the bottom of the column, a mixture is obtained having a propene content of not more than 50 ppm, preferably of not more than 10 ppm and still more preferably of not more than 5 ppm, and having a propylene oxide content of not more than 50 ppm, preferably of not more than 20 ppm and still more preferably of not more than 10 ppm, in each case based on the total weight of the mixture obtained at the bottom of the column.

At least part of the stream taken from the side of the dividing wall column can be recycled as solvent into stage (i) of the inventive process. Preferably, at least 90%, more preferably at least 95% of the stream taken from the side-offtake are recycled into stage (i).

Therefore, the present invention relates to a process as described above, wherein at least 90% of the stream taken from the side-offtake of the distillation column used in (ii) are recycled into stage (i).

The bottoms stream taken from the distillation column, preferably the dividing wall distillation column, essentially consisting of methanol, water and unreacted hydrogen peroxide, is then fed to the reactor of stage (iii). Preferably, the bottoms stream is cooled prior to being introduced into the reactor via, for example, one-stage cooling or two-stage cooling, more preferably to a temperature of from 20 to 40° C., still more preferably to a temperature of from 30 to 40° C. Still more preferably, fresh propene is additionally added directly into the reactor of stage (iii) or added to the bottoms stream obtained from (ii) prior to introducing same into the reactor of stage (iii). Alternatively or additionally, fresh hydrogen peroxide can be added.

The selectivity of this reaction in stage (iii) with respect to hydrogen peroxide is preferably in the range from 64 to 99%, more preferably in the range from 72 to 90% and particularly preferably in the range from 75 to 87%.

The selectivity of the overall process in stages (i) to (iii) with respect to hydrogen peroxide is preferably in the range from 78 to 99%, more preferably in the range from 88 to 97% and particularly preferably in the range from 90 to 96%.

The total hydrogen peroxide conversion is preferably at least 99.5%, more preferably at least 99.6%, more preferably at least 99.7% and particularly preferably at least 99.8%.

The reaction mixture obtained from stage (iii) preferably has a methanol content of from 50 to 90 wt.-%, more preferably of from 60 to 85 wt.-% and especially preferably of from 70 to 80 wt.-%, based on the total weight of the reaction mixture. The water content is preferably in the range of from 5 to 45 wt.-%, more preferably of from 10 to 35 wt.-% and especially preferably of from 15 to 25 wt.-%, based on the total weight of the reaction mixture. The propylene oxide content is preferably in the range of from 1 to 5 wt.-%, more preferably of from 1 to 4 wt.-% and especially preferably of from 1 to 3 wt.-%, based on the total weight of the reaction mixture. The propene content is preferably in the range of from 0 to 5 wt.-%, more preferably of from 0 to 3 wt.-% and especially preferably of from 0 to 1 wt.-%, based on the total weight of the reaction mixture.

The product mixture taken from the reactor of stage (iii) can be fed as mixture (GI) into stage (II) of the inventive process. Additionally, at least a portion of the stream taken from the top of the distillation column of stage (ii) can be combined with the product mixture taken from the reactor of stage (iii) to give mixture (GI) which is then fed into stage (II) of the inventive process. Alternatively, it is possible to separately feed the product mixture taken from the reactor of stage (iii) and at least a portion of the top stream of the distillation column of stage (ii) into stage (II), the latter embodiment wherein both streams are regarded as constituting mixture (GI) being preferred.

Therefore, according to a preferred embodiment of the present invention, mixture (GI) fed to stage (II) of the inventive process comprises of from 2 to 20 wt.-%, more preferably of from 5 to 15 wt.-% and still more preferably of from 8 to 13 wt.-% of propylene oxide, of from 1 to 10 wt.-%, more preferably of from 1.5 to 8 wt.-% and still more preferably of from 2 to 7 wt.-% of propene, and of from 0.005 to 3 wt.-%, more preferably of from 0.01 to 2 wt.-% and still more preferably of from 0.02 to 0.5 wt.-% of oxygen. The methanol content is preferably in the range of from 40 to 80 wt.-%, more preferably from 50 to 75 wt.-% and still more preferably from 60 to 70 wt.-%.

Stage (II)

According to stage (II) of the inventive process, propylene oxide is separated from mixture (GI) to give a mixture (GII) comprising propene and oxygen.

Separation according to (II) can be conducted by every suitable method. Most preferably, separation is conducted by distillation.

Separation according to stage (II) is preferably carried out in at least one distillation column, more preferably in one distillation column. Preferably, this column has of from 5 to 40, more preferably of from 10 to 35 and especially preferably of from 15 to 30 theoretical stages.

The distillation column is preferably operated at a top pressure of from 1 to 5 bar, more preferably of from 1 to 4 bar, more preferably of from 1 to 3 bar and still more preferably of from 1 to 2 bar such as 1, 1.1, 1.2, 1.3, 1.4, 1.5, 1.6, 1.7, 1.8, 1.9 or 2 bar.

According to the present invention, the mixture (GII) is obtained at the top of the distillation column comprising at least 80 wt.-%, more preferably at least 85 wt.-%, more preferably of from 85 to 97.5 wt.-% of propene, and from 0.5 to 7 wt.-%, more preferably from 0.5 to 2.5 wt.-%, more preferably from 0.5 to less than 2.5 wt.-%, more preferably from 0.5 to 2 wt.-% and still more preferably of from 0.5 to 1.5 wt.-% of oxygen.

In a preferred embodiment of the process according to the present invention, mixture (GII) which is obtained in step (II) and which is subjected to step (III) of the process according to the present invention is essentially free of argon, essentially free of $CF_4$ or essentially free of a mixture of these gases. Preferably, (GII) contains less than 100 ppm, more preferably less than 50 ppm and still more preferably less than 10 ppm of these gases. Even more preferably, the content of (GII) with respect to these gases is below the detection limit of the common analytical methods known to the skilled artisan.

In the context of the process of the present invention, it is possible to introduce propene into stage (i) or stage (iii) or stage (i) and (iii) as chemical grade propene in which propane is present in a volume ratio of propene to propane of from about 97:3 to about 95:5. In case chemical grade propene is used, the mixture (GII) can additionally comprise up to 15 wt.-%, preferably of from 5 to 10 wt.-% of propane, based on the total weight of mixture (GII).

Therefore, according to a preferred embodiment of the present invention, mixture (GII) obtained from (II) and fed to (III) comprises at least 80 wt.-%, more preferably at least 85 wt.-%, more preferably of from 85 to 97.5 wt.-% of propene, of from 0.1 to 15 wt.-%, more preferably of from 0.1 to 12 wt.-% and still more preferably of from 0.1 to 10 wt.-% of propane, and from 0.1 to 7 wt.-%, such as, for example, from 0.1 to less than 0.5 wt.-%, preferably from 0.1 to 0.45 wt.-%, more preferably from 0.15 to 0.4 wt.-%, or, for example, from 0.5 to 7 wt.-%, preferably from 0.75 to 6 wt.-%, more preferably from 1.0 to 5 wt.-% of oxygen.

Therefore, the process of the present invention is especially suitable to remove oxygen from mixtures having a propene content of more than 75 wt.-%, particularly far more than 75 wt.-% such as at least 80 wt.-%, preferably from 85 to 97.5 wt.-%.

Still more preferably, the mixture (GII) is essentially free of carbon monoxide as additional compound subjected to oxidation. Preferably, (GII) contains less than 100 ppm, more preferably less than 50 ppm and still more preferably less than 10 ppm of carbon monoxide.

The evaporator of the distillation column used in stage (II) of the inventive process is at least partially operated with at least a part of (Td), (Td) being described hereinabove.

According to a further embodiment of the present invention, at least one feed stream fed into stage (II) is heated with the bottoms stream obtained from the column used in stage (II).

According to one embodiment of the present invention, (GII) as obtained from stage (II) is fed into stage (III). This process is carried out preferably in cases where (GII) as obtained from stage (II) has an oxygen content in the range of from 0.5 to 7 wt.-%, more preferably in the range of from 0.75 to 6 wt.-%, and still more preferably in the range of from 1.0 to 5 wt.-%.

According to another embodiment, (GII) as obtained from stage (II) is subjected to at least one suitable intermediate stage before it is fed into stage (III). Especially preferred is an intermediate stage in which the oxygen concentration of (GII) is increased. This process is carried out preferably in cases where (GII) as obtained from stage (II) has an oxygen content in the range of from 0.1 to less than 0.5 wt.-%, more preferably in the range of from 0.1 to 0.45 wt.-%, and still more preferably in the range of from 0.15 to 0.40 wt.-%. Preferably, the oxygen content of these mixtures is increased so that the oxygen content of the mixture fed into stage (III) is in the range of from 0.5 to 7 wt.-%, more preferably in the range of from 0.75 to 6 wt.-%, and still more preferably in the range of from 1.0 to 5 wt.-%.

According to a preferred embodiment of the present invention, this intermediate stage comprises, more preferably consists of compressing, cooling and condensing the gaseous stream (GII) obtained from (II). Preferably the gaseous stream (GII) obtained from (II) is compressed from a pressure of from 1 to 5 bar to a pressure of from 15 to 20 bar in from 1 to 10 such as 1, 2, 3, 4, 5, 6, 7, 8, 9, or 10 compressing stages. Surprisingly, it was found that this intermediate stage allows for separating a major portion of the methanol and/or a major portion of the propene comprised in (GII) as obtained from (II) wherein this separation is achieved by condensation, preferably at condensation temperature of from 35 to 45° C. It was surprisingly found that methanol which is possibly contained in (GII) in amounts of, for example, 0.1 to 5.0 wt.-%, based on the total weight of (GII), said methanol being obtained by such condensation, has such a low oxygen concentration that it can be recycled without further purification into the process, for example as solvent or as part of the solvent mixture of stage (i) and/or (iii) of the present invention. Moreover, it was surprisingly found that propene obtained by such condensation has such a low oxygen concentration that it can be recycled without further purification into the process, for example as starting material of stage (i) and/or (iii) of the present invention.

Therefore, the present invention also relates to a process as described above wherein between stages (II) and (III), the mixture (GII) obtained from (II) is subjected to at least one intermediate compression stage wherein the pressure of (GII) is increased from a value of 1 to 5 bar to a value of 15 to 20 bar.

Accordingly, the present invention also relates to a process as described above wherein between stages (II) and (III), the mixture (GII) obtained from (II) is subjected to at least one compression stage wherein the pressure of (GII) is increased from a value of 1 to 5 bar to a value of 15 to 20 bar, and wherein methanol is at least partially separated by at least one cooling and condensing stage.

Accordingly, the present invention also relates to a process as described above wherein between stages (II) and (III), the mixture (GII) obtained from (II) is subjected to at least one compression stage wherein the pressure of (GII) is increased from a value of 1 to 5 bar to a value of 15 to 20 bar, and wherein methanol is separated by at least one cooling and condensing stage, and wherein the methanol stream thus obtained has an oxygen content low enough to allow for recycling the separated methanol stream into stage (i) and/or (iii).

Accordingly, the present invention also relates to a process as described above wherein between stages (II) and (III), the mixture (GII) obtained from (II) is subjected to at least one compression stage wherein the pressure of (GII) is increased from a value of 1 to 5 bar to a value of 15 to 20 bar, and wherein propene is at least partially separated by at least one cooling and condensing stage.

Accordingly, the present invention also relates to a process as described above wherein between stages (II) and (III), the mixture (GII) obtained from (II) is subjected to at least one compression stage wherein the pressure of (GII) is increased from a value of 1 to 5 bar to a value of 15 to 20 bar, and wherein propene is separated by at least one cooling and condensing stage, and wherein the propene stream thus obtained has an oxygen content low enough to allow for recycling the separated methanol stream into stage (i) and/or (iii).

Accordingly, the present invention also relates to a process as described above wherein between stages (II) and (III), the mixture (GII) obtained from (II) is subjected to at least one compression stage wherein the pressure of (GII) is increased from a value of 1 to 5 bar to a value of 15 to 20 bar, and wherein methanol and propene are at least partially separated by at least one cooling and condensing stage.

Accordingly, the present invention also relates to a process as described above wherein between stages (II) and (III), the mixture (GII) obtained from (II) is subjected to at least one compression stage wherein the pressure of (GII) is increased from a value of 1 to 5 bar to a value of 15 to 20 bar, and wherein methanol and propene are separated by at least one cooling and condensing stage, and wherein the methanol stream and propene stream thus obtained have an oxygen content low enough to allow for recycling the separated methanol stream and propene stream into stage (i) and/or (iii).

Thus, the process invention also relates to a process as described above, wherein the mixture (GII) subjected to (III) comprises of from 0.5 to 7 wt.-%, preferably of from 0.75 to 6 wt.-% and more preferably of from 1.0 to 5 wt.-% of oxygen, 80 to 97.5 wt.-%, more preferably of from 85 to 97.5 wt.-% of propene, and of from 0.1 to 20 wt.-%, preferably of from 0.2 to 15 wt.-%, more preferably of from 0.5 to 10 wt.-% of propane, in each case based on the total weight of the mixture (GII).

Stage (III)

According to stage (III) of the inventive process, the oxygen comprised in mixture (GII) is at least partially reduced by addition of and reaction with hydrogen to mixture (GII) in the presence of a catalyst comprising copper in elemental and/or oxidic form on a support, wherein copper is present on the support in an amount of 30 to 80 wt.-% based on the whole catalyst and calculated as CuO.

It has surprisingly been found that a catalyst comprising copper in elemental and/or oxidic form on a support, wherein copper is present on the support in an amount of 30 to 80 wt.-% based on the whole catalyst and calculated as CuO, can be used under suitable conditions as catalyst for reducing oxygen with hydrogen in the presence of propene, preferably also in the presence of propane.

Generally, it is found that this type of catalyst can be used under suitable conditions as catalyst for reducing oxygen with hydrogen in the presence of unsaturated compounds, preferably alkenes, preferably also in the presence of the saturated compounds corresponding to the unsaturated compounds, preferably the alkanes corresponding to the alkenes, such as propane corresponding to propene.

According to a preferred embodiment, the catalyst used in (III) comprises copper in elemental and/or oxidic form on at least one suitable catalyst support. As catalyst supports, oxide supports or any other suitable supports are to be mentioned. Most preferred are oxide supports. As oxide supports, silicon oxides, zirconium oxides, aluminium oxides, niobium oxides, titanium oxides, magnesium oxides, zinc oxides, lanthanum oxides, cerium oxides, tin oxides, clay or the like, molecular sieves such as zeolites, suitable silicates such as alkali silicates or alkaline earth silicates, or mixtures of two or more of theses oxides are preferred. The support may be amorphous, crystalline, or amorphous as well as crystalline. Moreover, the support may have a porous structure or comprise at least one porous domain, wherein the porous structure or the at least one porous domain may comprise micropores, mesopores, macropores, micro- and mesopores, micro- and macropores, meso- and macropores, or micro-, meso- and macropores. Most preferably, the support is an inert support with regard to the reduction reaction of (III).

In a preferred embodiment of process according to the present invention, the support of the catalyst employed in (III) is an inorganic material comprising silicon, oxygen, and at least one element chosen from the group consisting of alkali metals and alkaline earth metals, preferably alkaline earth metals, and most preferably magnesium.

According to a still further preferred embodiment, the support comprises an inert metal silicate selected from the group of alkali metal silicates and alkaline earth metal silicates, preferably alkaline earth metal silicates.

Therefore, the present invention relates to a process as described above wherein the catalyst employed in (III) comprising copper in elemental and/or oxidic form comprises an alkaline earth metal silicate support.

According to a still further preferred embodiment, the present invention relates to a process as described above wherein the alkaline earth silicate support comprises magnesium silicate.

More preferably, the catalyst support of the catalyst employed in (III) comprises at least 90 wt.-%, more preferably at least 95 wt.-%, more preferably at least 96 wt.-%, more preferably at least 97 wt.-%, more preferably at least 98 wt.-% and still more preferably at least 99 wt.-% of magnesium silicate, based on the total weight of the support. Especially preferably, the catalyst support essentially consists of magnesium silicate.

Therefore, the present invention relates to a process as described above, wherein in the catalyst employed in (III), the support is magnesium silicate according to (idealized) formula $MgSiO_3$.

The catalyst employed in (III) comprising copper in elemental and/or oxidic form comprises a support, as described above, preferably a silicate, more preferably an alkaline earth silicate, still more preferable an alkaline earth silicate comprising magnesium silicate, still more preferably magnesium silicate.

Therefore, the present invention relates to a process as described above, wherein in the catalyst employed in (III) is a supported catalyst, the support comprising at least 90 wt.-% of magnesium silicate, preferably consisting essentially of magnesium silicate.

Preferably, the catalyst, in its calcined state, has a BET surface determined according to DIN 66131 in the range of from 100 to 400 $m^2/g$, more preferably of from 150 to 400 $m^2/g$, more preferably of from 150 to 350 $m^2/g$, more preferably of from 200 to 320 $m^2/g$ and still more preferably of from 200 to 300 $m^2/g$. Generally, these ranges refer to the fresh catalyst employed in (III). Especially for continuously operated reactions according to stage (III) of the present invention, it was found that the BET surface of the fresh catalyst according to the invention changes during the course of the reaction. Typically, the BET surface decreases during the course of the reaction. For example, it was found that after a reaction period of 200 h or more such as 500 h or more or 1000 h or more, the BET surface will be below 100 $m^2/g$, preferably in the range of from 10 to 70 $m^2/g$, more preferably from 20 to 60 $m^2/g$ such as from 30 to 50 $m^2/g$.

Surprisingly, it was found that the catalyst employed according to the present invention having, as fresh catalyst, BET surfaces in above-mentioned ranges, will exhibit excellent characteristics after said reaction periods of 200 h or more such as 500 h or more or 1000 h although its BET surface changes, and even may dramatically change during the course of the reaction. Taken into account that it is a well-known fact that the BET surface of a catalyst has a significant influence on the catalytic characteristics of a catalyst, this shows the superior aptitude of the catalyst for the inventive process.

Consequently, this advantageous long-term characteristics of the catalyst of the present invention further makes it possible to employ a freshly prepared catalyst or, if desired, a suitably pre-aged catalyst having lower BET surfaces such as BET surfaces in above-mentioned lower ranges of below 100 $m^2/g$, such as from 10 to 70 $m^2/g$, from 20 to 60 $m^2/g$, or from 30 to 50 $m^2/g$. It is further conceivable to employ, in stage (III), a catalyst which, as freshly prepared (and calcined) catalyst has BET surfaces in above-mentioned lower ranges of below 100 $m^2/g$, such as from 10 to 70 $m^2/g$, from 20 to 60 $m^2/g$, or from 30 to 50 $m^2/g$.

Therefore, the present invention also describes the use of a catalyst comprising copper in elemental and/or oxidic form on a support, wherein copper is present on the support in an amount of 30 to 80 wt.-% based on the whole catalyst and calculated as CuO for improving the long-term operating time of a preferably continuously operated reaction, wherein the oxygen contained in a mixture comprising propene and oxygen is reduced by adding hydrogen to said mixture in the presence of said catalyst.

Especially preferred operating times achieved are at least 200 h, preferably at least 500 h, more preferably at least 1000 h. The term "operating time" relates to the time during which the employed catalyst is not replaced or subjected to a regeneration process.

The catalyst according to the present invention is preferably employed as molding. Preferred geometries are, for example, pellet, ring-shaped pellet, sphere such as compact or hollow sphere, cylinder, conus, frustum, strand such as star-shaped strand or cog-wheel-shaped strand. The mean diameter of preferred geometries is preferably 0.5 to 10 mm, more preferably 1 to 8 mm and especially preferably 3 to 6 mm.

Most preferred geometries are spheres and cylinders, and especially preferred are cylinders. Preferably, not more than 5 wt.-% of the cylinders have a diameter of less than 3 mm, and not more than 5 wt.-% of the cylinders have a diameter of more than 6 mm.

Therefore, copper in elemental form or in oxidic form or in elemental as well as in oxidic form is preferably supported on a support, preferably a support as described above, more preferably a silicate support and in particular a magnesium silicate support, so that the BET surface of the final calcined catalyst, determined according to DIN 66131, is most preferably in the range of from 200 to 300 $m^2/g$.

According to an especially preferred embodiment, copper is the sole catalytically active metal in the catalyst employed in (III).

In addition to copper, the catalyst employed in (III) further comprises at least one promoter chosen from groups 1, 2, 3, 4, 5, 6, 7, 8, 9, 10, 11 or 12 (new IUPAC nomenclature) of the Periodic Table of the Elements. Preferably, the at least one promoter is chosen form the group consisting of Li, Na, K, Rb, Cs, Be, Ca, Sr, Ba, Sc, Ti, V, Nb, Cr, Mo, W, Mn, Fe, Co, Ni, Zn and mixtures of one or more of these elements.

Therefore, the present invention also relates to a process as described above, wherein catalyst employed in stage (III) of the present inventive process comprises copper in elemental and/or oxidic form and further comprises at least on promoter chosen from groups 1, 2, 3, 4, 5, 6, 7, 8, 9, 10, 11 or 12 (new IUPAC nomenclature) of the periodic table of the elements, preferably being supported on a silicate, most preferably magnesium silicate.

In general, the amount of copper in elemental and/or oxidic form comprised in the catalyst employed in stage (III) of the present invention is 30 to 80 wt.-%, preferably 30 to 70 wt.-%, more preferably 35 to 60 wt.-%, more preferably from 40 to 50 wt.-%, in each case based on the whole catalyst and calculated as CuO, comprising copper in elemental and/or oxidic form and optionally at least one promoter, and calculated as CuO, on the support, preferably a silicate, more preferably magnesium silicate.

If at least one promoter chosen form the group as mentioned above is present in the catalyst employed in stage (III), the total amount of the at least one promoter as described above, is preferably less than 10 wt.-%, more preferably less than 6 wt.-%, most preferably less than 4 wt.-%, in each case based on the whole catalyst, comprising copper in elemental and/or oxidic form and the at least one promoter, and calculated as the corresponding oxides.

According to even more preferred embodiments, the catalyst employed in (III), in addition to Cu, contains at least one element chosen from the group consisting of Cr, Zn, and Ba.

According to a preferred embodiment, the catalyst employed in stage (III) of the process according to the present invention has a barium content calculated as barium oxide (BaO) of less than 4 wt.-%, more preferably less than 3 wt.-%, most preferably less than 2.5 wt.-%, and still more preferably less than 2 wt.-%, in each case based on the total weight of the catalyst.

According to a preferred embodiment, the catalyst employed in stage (III) of the process according to the present invention has a chromium content calculated as chromium oxide ($Cr_2O_3$) of less than 4 wt.-%, more preferably less than 3 wt.-%, most preferably less than 2.5 wt.-%, more preferably less than 2 wt.-%, and still more preferably less than 1 wt.-%, in each case based on the total weight of the catalyst.

According to a preferred embodiment, the catalyst employed in stage (III) of the process according to the present invention has a zinc content calculated as zinc oxide (ZnO) of less than 4 wt.-%, more preferably less than 3 wt.-%, most preferably less than 2.5 wt.-%, more preferably less than 2 wt.-%, and still more preferably less than 1.5 wt.-%, in each case based on the total weight of the catalyst.

According to a still more preferred embodiment the catalyst employed in stage (III) of the process according to the present invention has a content of Ba, Cr and Zn, in sum and calculated as corresponding oxides, as defined above, of less than 8 wt.-%, more preferably less than 6 wt.-%, more preferably less than 5 wt.-%, more preferably less than 4 wt.-%, more preferably 0.1 to 3 wt.-%, and in particular from 1 to 3 wt.-%, in each case based on the total weight of the catalyst.

Therefore, the present invention also relates to a process as described above, wherein the catalyst employed in stage (III) has a barium content of less than 2 wt.-%, a chromium content of less than 2 wt.-% and a zinc content of not more than 1.5 wt.-%, in each case calculated as the corresponding oxides, as defined above, based on the total weight of the catalyst.

The catalyst which is preferably employed in stage (III) of the process according to the present invention has a preferred loss of attrition of less than 5 wt.-%, preferably less than 4 wt.-%, and more preferably less than 3 wt.-%. In the context of the present invention, abrasion values are determined according to ASTM D 4058-81.

Further, the catalyst which is preferably employed in stage (III) of the process according to the present invention has a preferred crush strength of more than 5 N, preferably more than 6 N, and more preferably more than 7 N. In the context of the present invention, the crush strength is determined on a test apparatus Z2.5 (Zwick Company).

Therefore, in a preferred aspect of the present invention, preferably a catalyst is employed in stage (III) of the process as described above having a preferred loss of attrition of less than 3 wt.-% and preferred crush strength of more than 5 kg.

The catalyst's mean bulk density is preferably in the range of from 0.3 to 2 $g/cm^3$, more preferably of from 0.6 to 1.2 $g/cm^3$.

The catalysts which are used in stage (III) of the process according to the present invention can be obtained by any process for the preparation of said catalysts that is known to a person having ordinary skill in the art.

For example, the catalysts can be obtained by co-precipitation of precursor compounds from solution or dispersion, immersing the support material in a solution or dispersion of precursor compounds of the metals being present on the support, dry blending of metal oxides which are present in the catalyst etc., preferably followed by drying, calcinations and/or reduction.

In a preferred embodiment, the catalyst which can be used in stage (III) of the process according to the present invention are prepared by precipitating the support material, for example alkali earth metal silicate, preferably magnesium silicate, by adding a solution of the alkali earth metal, preferably a magnesium salt solution, particularly preferred a magnesium nitrate solution, to an alkali metal silicate solution which is advantageously strongly alkaline, preferably a waterglass solution, the ratios of the salt solutions to be reacted advantageously being chosen so that the precipitate which contains alkali earth metal and silicate, preferably magnesium and silicate, calculated as oxides of alkali earth metal and silicon, preferably MgO and $SiO_2$, in the desired molar ratio. The precipitate obtained in the reaction of alkali earth metal solution with alkali metal silicate solution, preferably magnesium salt solution with the waterglass solution, is preferably X-ray amorphous.

Copper and, if desired, further components, particularly preferred zinc, chromium and/or barium in the form of their salt solutions, preferably in the form of their nitrate solutions, are then added to the resulting support material suspension, preferably to the magnesium silicate suspension, advantageously with stirring. A precipitating agent can be metered into this mixture before or after the addition of this metal salt solution but is advantageously introduced simultaneously with the metal salt solutions into the precipitation apparatus. The precipitating agents used are in general aqueous solutions of the hydroxides, carbonates or bicarbonates of the alkali metals. The use of sodium carbonate or potassium carbonate solutions as precipitating agents is particularly preferred. Precipitation may be carried out at room temperature, at elevated temperatures or at the boiling point. It is advantageously effected at from 30° C. to 70° C.

In the preparation of the catalysts used according to the present invention, it is also possible to employ a method in which the support material, preferably magnesium silicate, and the other catalyst components are precipitated separately and the resulting precipitates are mixed before or after drying, but the procedure described above, in which the stated catalyst components are precipitated onto the precipitated support material, preferably magnesium silicate, is preferred.

In the preparation of zinc-containing catalysts with the use of alkali metal hydroxide solutions as precipitating agents, it is of course necessary to ensure that the precipitated zinc hydroxide does not redissolve as zincate owing to the addition of excessive amounts of alkali metal hydroxide. In the preparation of chromium-containing catalysts, water-soluble chromium(III) salts are preferably used as starting materials.

The generally chemically impure precipitate of the catalyst components which is obtained in this manner comprises a mixture of sparingly soluble hydroxides, carbonates, hydrated oxides and basic salts of the precipitated metal components with the support material, preferably the magnesium silicate mixture, precipitated beforehand, the composition of said precipitate depending on the precipitating agent used.

The precipitated catalyst components can be separated from the liquid phase in a conventional manner, for example by filtration or centrifuging, and washed and dried. The drying temperature is in general from 80° C. to 200° C., preferably from 100° C. to 160° C., in particular from 110° C. to 130° C. After drying, the catalyst is calcined, in general at from 200° C. to 500° C. For the preparation of catalyst moldings, the calcined catalyst raw material is advantageously thoroughly mixed with molding assistants, such as graphite or stearic acid, and then pressed to give the desired moldings.

All catalyst properties discussed above, such as BET surface or the like, relate to the catalyst in its calcined state.

Before they are used in step (III) of the process of the present invention, the catalysts may be reduced in a stream of hydrogen at elevated temperatures. The hydrogen is preferably used in the form of a gas mixture of hydrogen and an inert gas, such as nitrogen or argon. The reduction of the catalyst is generally carried out at 150° C. to 250° C. In the reduction, the metal components reducible with hydrogen are reduced to the metals if they come into contact with the reducing agent directly or by diffusion. The catalysts which can be used according to the invention can be employed as a powder or as moldings for the reaction.

According to a preferred embodiment of the present invention, the catalyst, prepared as described above, is not subjected to a hydrogen stream prior to its use in step (III).

In a very preferred embodiment, the catalyst which is used in stage (III) of the process according to the present invention, is prepared in accordance with the method disclosed in EP 0 427 062 A2, preferably according page 3, lines 4 to 38, in particular according to the example, catalyst 2, page 4, lines 41 to 50.

According to stage (III) of the process according to the present invention, the mixture (GII) comprising oxygen obtained from (II), optionally after at least one intermediate stage as described above, is reacted with hydrogen.

Surprisingly, it was found that in (III), oxygen can be effectively removed from (GII) by adjusting the molar hydrogen:oxygen ratio at values which are smaller than 5:1, preferably smaller than or equal to 4.5:1, more preferably smaller than or equal to 4.0:1, more preferably smaller than or equal to 3.5:1. Still more preferably, the molar hydrogen:oxygen ratio is in the range from 0.1:1 to 4.5:1, more preferably from 0.2:1 to 4.0:1, more preferably from 0.3:1 to 3.5:1.

According to one embodiment of the present invention, the molar hydrogen:oxygen ratio is preferably from 0.4:1 to 3.0:1, more preferably from 0.5:1 to 3.0:1, more preferably from 0.6:1 to 2.0:1 and still more preferably from 0.7:1 to 1.5:1.

According to another embodiment of the present invention, the molar hydrogen:oxygen ratio is preferably from 1.5:1 to 4.0:1, more preferably from 2.0:1 to 4.0:1, more preferably from 2.0:1 to 3.5:1 and still more preferably from 2.5:1 to 3.5:1.

Therefore, it was found that the removal of oxygen may be achieved in the presence of comparatively low concentrations of hydrogen. Since oxygen is effectively removed from (GII), the conversion of hydrogen in (III) is at least 30%, more preferably at least 40%, more preferably at least 50%, more preferably at least 60% and still more preferably at least 70%.

Preferred oxygen conversion of the present invention according to stage (III) are at least 90%, more preferably at least 95%, more preferably at least 97%, more preferably at least 98%, and still more preferably at least 99%.

The reaction of oxygen in (GII) with hydrogen in stage (III) is preferably carried out at a pressure from 0.1 to 100 bar, more preferably from 0.5 to 50 bar, more preferably from 0.6 to 30 bar.

In an industrial scale, it was found that pressures in the range of from 10 to 100 bar are preferred, preferably from 10 to 80 bar, more preferably from 10 to 60 bar, more preferably from 10 to 40 bar, more preferably from 10 to 20 bar.

The temperature at which the reaction in (III) is carried out is preferably at least 100° C., more preferably at least 125° C., more preferably at least 150° C. and more preferably at least 175° C. Thus, preferred ranges of the temperature at which the reaction in (III) is carried out are from 100 to 500° C., preferably from 150 to 400° C., more preferably from 175 to 350° C., more preferably from 175 to 300° C., and still more preferably from 175 to 250° C.

The reactor in which stage (III) of the process according to the present invention is conducted and the respective reaction conditions are preferably chosen so that the maximum temperature within the catalyst bed is preferably below 350° C., more preferably below 300° C., still more preferably below 250° C. A person having ordinary skill in the art does know how to conduct stage (III) of the present process in a way to obtain the desired reaction temperatures but not to obtain higher temperatures than mentioned in the catalyst bed. For example, the maximum temperature in the catalyst bed can be measured with a plurality of thermo elements. In case a tubular reactor is employed in stage (III) of the present process, thermo elements are preferably placed along the axis of the catalyst bed and the thermo elements and/or the surrounding thermowell may preferably have a diameter less than one third of the diameter of the reactor used.

Therefore, the reaction in (III) is preferably carried out at a pressure from 0.1 to 100 bar and a temperature of at least 100° C. such as from 100 to 400° C., more preferably a pressure from 10 to 20 bar and a temperature of at least 175° C. According to an especially preferred embodiment of the present invention, the reaction in (III) is carried out at a pressure from 10 to 80 bar and a temperature from 175 to 350° C., more preferably at a pressure from 10 to 60 bar and a temperature from 175 to 350° C., more preferably at a pressure from 10 to 40 bar and a temperature from 175 to 300° C. and still more preferably at a pressure from 10 to 20 bar and a temperature from 175 to 250° C.

As pointed out, keeping the temperatures in the desired ranges may be achieved by any suitable method, for example via suitable internal cooling means or suitable external cooling means of combined suitable internal and external cooling means, wherein any suitable cooling medium or mixture of cooling media may be employed. Moreover, the temperature difference between the point where a given cooling medium enters a cooling means and the point where said cooling medium leaves said cooling means may be suitably chosen, for example via flow rate of the cooling medium and/or flow direction of the cooling medium.

It was surprisingly found that the specific reaction conditions and the use of the catalyst comprising copper in elemental and/or oxidic form and optionally at least one promoter, allow for an extremely low propene conversion. Preferably, the conversion of propene into propane and/or by-products such as carbon dioxide is less than 5%, more preferably less than 4%, more preferably less than 3%, more preferably less than 2% and still more preferably less than 1%, and even more preferably less than 0.5%.

Hydrogen may be added to mixture (GII) as pure or essentially pure hydrogen. Alternatively, hydrogen may be added to (GII) as a mixture of hydrogen and at least one other, most preferably inert compound. The term "inert compound" as used in this specific context relates to a compound which does not react with hydrogen in stage (III) of the present invention or which reacts with hydrogen to a negligible extent compared to the reaction of hydrogen with oxygen and thus has essentially no influence on the reaction according to (III). Examples of such inert compounds are nitrogen, argon, methane, ethane, propane, propene, water, or the like. In this context, it is conceivable that a mixture of propene, propane and water is employed which is obtained from a suitable propane dehydrogenation process, optionally comprising, after the dehydrogantion, at least one downstream work-up stage. Most preferably, hydrogen is added to (GII) as pure or essentially pure compound. In case a mixture essentially consisting of hydrogen and water is used, the water content of said mixture can be in the range of from 0.1 to 15 wt.-% such as from 1 to 10 wt.-% or from 5 to 10 wt.-%, based on the total weight of the mixture. Water can be employed as steam and/or liquid.

The reaction according to (III) can be carried out in one, two, three or more reactors two or more of which optionally serially coupled and/or operated in parallel. The mixture (GII) which is fed to a reactor can be mixed with hydrogen and/or a mixture comprising and at least one other, most preferably inert compound, prior to being fed into the reactor. Alternatively and/or additionally, a separate stream of hydrogen or a mixture of hydrogen and at least one other, most preferably inert compound can be separately fed into the reactor.

According to a preferred embodiment of the present inventive process, the feed stream into the reactor, prior to being fed into the reactor, is brought to a temperature of at least 100° C., more preferably to a temperature from 100 to 300° C., more preferably from 150 to 300° C. and still more preferably from 175 to 250° C.

By way of example, some of conceivable alternatives are listed which apparatus may be used for the reaction according to stage (III) of the inventive process:

According to one alternative, the reaction according to (III) can be performed in a Linde-type isothermal reactor wherein the shell compartment is filled with the fixed-bed catalyst as described above, and a stream of (GII) and hydrogen or the hydrogen containing mixture passes through the fixed-bed in downflow or upflow mode, more preferably in downflow mode. At least one cooling agent is passed through the cooling coils of the reactors. As cooling agents, water and/or oil may be used. If water is used as cooling agent, it can be used for the generation of steam subsequently after having passed through the coils.

According to another alternative, the reaction according to (III) can be performed in a heat exchanger operated with air as cooling medium wherein vertical or horizontal configurations are conceivable where the cooling air is either drawn into the apparatus or pressed into the apparatus (see FIGS. 1 to 4). According to this embodiment, the tubes are filled with catalyst, and cooling is performed via the outer compartment.

Figure 5:
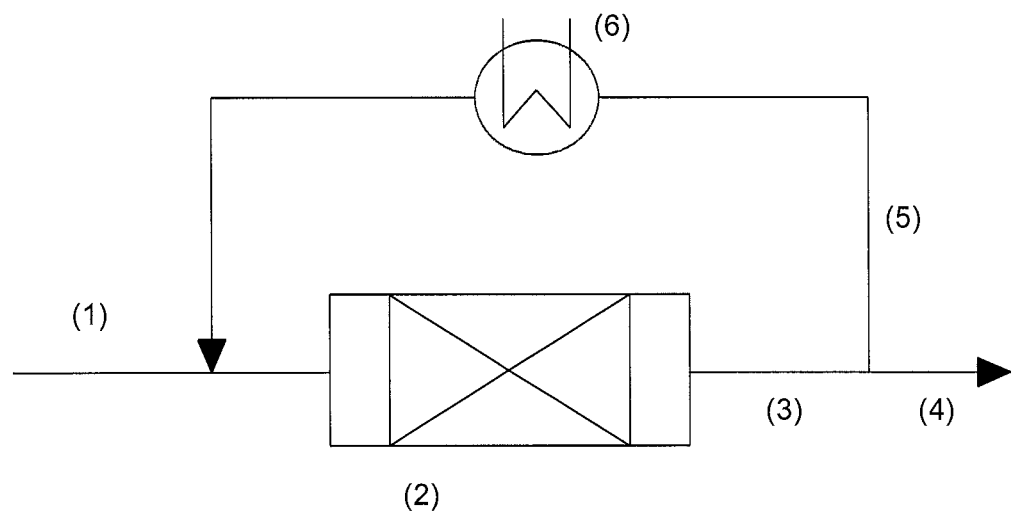

According to another alternative, the reaction according to (III) can be performed in an adiabatic fixed-bed shaft reactor with back-mixing without direct cooling of the reaction mixture (see FIG. 5). According to this embodiment, the feed is mixed with at least a portion of the product stream prior to being fed into the reactor in such a way that the adiabatic temperature increase is below a chosen critical value, for example at most 100° C., preferably at most 90° C., more preferably at most 80° C. and still more preferably at most 70° C.

According to yet another alternative, the reaction according to (III) can be performed in a tube bundle reactor. As far as tube bundle reactors are concerned, conceivable reactor designs are described, for example, in DE 202 19 277 U1, DE 202 19 278 U1, or DE 202 19 279 U1.

Depending on specific needs of the inventive process, at least two of the above-described apparatuses can be suitably combined. It is possible to combine at least two shaft reactors such as two or three or more shaft reactors or to combine at least two heat exchangers such as two or three or more heat exchangers or to combine at least two Linde-type isothermal reactors such as two or three or more Linde-type isothermal reactors. If necessary, it is also possible to combine at least one shaft reactor with at least one heat exchanger or to combine at least one shaft reactor with at least one Linde-type isothermal reactor or to combine at least one heat exchanger with at least one Linde-type isothermal reactor. If two or more apparatuses are combined, it is possible to couple at least two of the apparatuses serially and/or at least two of the apparatuses in parallel. If two or more apparatuses are serially coupled and at least two of the apparatuses are principally different from each other, the type of reactor into which (GII) is fed subsequently after stage (III) can be freely chosen. If, e.g., a shaft reactor is serially coupled with a heat exchanger, (GII) can be fed into the shaft reactor first, the product stream of which then being at least partially fed into the heat exchanger. It is also possible to feed (GII) into the heat exchanger first, the product stream then being at least partially fed into the shaft reactor. If, e.g., a shaft reactor is serially coupled with a Linde-type reactor, (GII) can be fed into the shaft reactor first, the product stream of which then being at least partially fed into the Linde-type reactor. It is also possible to feed (GII) into the Linde-type reactor first, the product stream then being at least partially fed into the shaft reactor. If, e.g., a Linde-type reactor is serially coupled with a heat exchanger, (GII) can be fed into the Linde-type reactor first, the product stream of which then being at least partially fed into the heat exchanger. It is also possible to feed (GII) into the heat exchanger first, the product stream then being at least partially fed into the Linde-type reactor.

Figure 7:
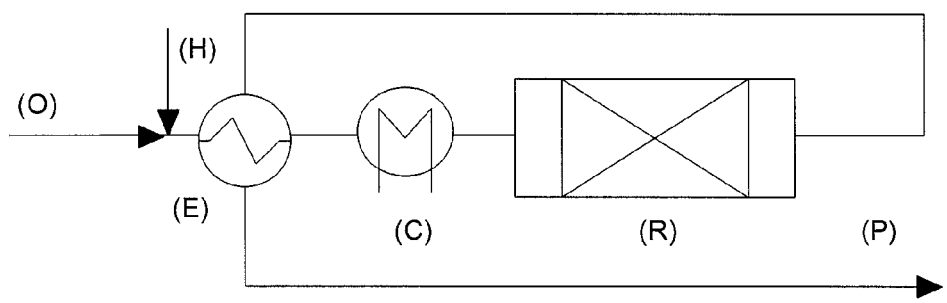

According to another alternative, mixture (GII) is fed into a cascade of at least two serially coupled fixed-bed shaft reactors such as two, three, four or more serially coupled fixed-bed shaft reactors, more preferably two or three serially coupled fixed-bed shaft reactors and especially preferably three serially coupled fixed-bed shaft reactors (see FIG. 7).

Therefore, the present invention also relates to a process as described above, wherein in (III), reduction of the oxygen is carried out in at least two serially coupled reactors, preferably shaft reactors, more preferably fixed-bed shaft reactors, still more preferably two or three fixed-bed shaft reactors and especially preferably three fixed-bed shaft reactors.

According to one alternative, the at least two shaft reactors are equipped with an external or internal cooling device. According to another alternative, which is preferred, at least one of the shaft reactors, preferably all shaft reactors are designed as adiabatic reactors. As to this preferred embodiment, it is still more preferred that at least one product stream leaving a given reactor is cooled after having left the reactor. Still more preferably, each product stream leaving a given reactor is cooled prior to being fed into the next reactor and/or being fed to a further stage of the inventive process.

Cooling of a stream can be performed according to any suitable method. Especially preferred is cooling via at least one heat exchanger. Alternatively and/or additionally, a stream which is to be fed into a given reactor can be cooled or brought to a desired temperature prior to being fed into the reactor by addition of a further stream such as especially preferably a stream comprising hydrogen.

Therefore, according to this embodiment of the present invention, the mixture (GII) leaving stage (II) of the inventive process is heated to a temperature of from 100 to 300° C., more preferably from 150 to 300° C. and still more preferably from 150 to 250° C. prior to being fed into the first reactor of the cascade of at least two serially coupled fixed-bed shaft reactors. Prior to being fed into the said first reactor, a stream comprising hydrogen, preferably a stream essentially consisting of hydrogen, is added to (GII).

Most preferably, the amount of hydrogen added is adjusted so that the molar ratio of hydrogen:oxygen is smaller than 5, preferably smaller than or equal to 4.5, more preferably smaller than or equal to 4.0, more preferably smaller than or equal to 3.5, more preferably smaller than or equal to 3.0. Still more preferably, the molar hydrogen:oxygen ratio is in the range from 0.1:1 to 4.5:1, more preferably from 0.2:1 to 4.0:1, more preferably from 0.3:1 to 3.5:1, more preferably from 0.4:1 to 3.0:1, more preferably from 0.5:1 to 3.0:1, more preferably from 0.6:1 to 2.0:1 and still more preferably from 0.7:1 to 1.5:1.

The pressure and temperature of the reaction in the first reactor are preferably adjusted so that the adiabatic temperature increase in the first reactor does not exceed 100° C., preferably 90° C., more preferably 80° C. and still more preferably 70° C. Most preferably, the pressure at which the reaction in the first reactor is carried out, is in the range from 10 to 100 bar, more preferably from 10 to 80 bar, more preferably from 10 to 60 bar, more preferably from 10 to 40 bar, and still more preferably from 10 to 20 bar.

The product stream leaving the first reactor is then fed to the second reactor of the cascade. Prior to being fed into the second reactor, the product stream is preferably brought to a temperature of from 100 to 300° C., more preferably from 150 to 300° C. and still more preferably from 150 to 250° C. If necessary, a stream comprising hydrogen, preferably a stream essentially consisting of hydrogen, is added to the product stream leaving the first reactor. Most preferably, the amount of hydrogen added is adjusted so that the molar ratio of hydrogen:oxygen is smaller than 5, preferably smaller than or equal to 4.5, more preferably smaller than or equal to 4.0, more preferably smaller than or equal to 3.5, more preferably smaller than or equal to 3. Still more preferably, the molar hydrogen:oxygen ratio is in the range from 0.1:1 to 4.5:1, more preferably from 0.2:1 to 4.0:1, more preferably from 0.3:1 to 3.5:1, more preferably from 0.4:1 to 3.0:1, more preferably from 0.5:1 to 3.0:1, more preferably from 0.6:1 to 2.0:1 and still more preferably from 0.7:1 to 1.5:1. Thus, if the product stream leaving the first reactor comprises an amount of hydrogen in the preferred ranges, it is not necessary to add an additional stream comprising hydrogen.

The pressure and temperature of the reaction in the second reactor are preferably adjusted so that the adiabatic temperature increase in the second reactor does not exceed 100° C., preferably 90° C., more preferably 80° C. and still more preferably 70° C. Most preferably, the pressure at which the reaction in the second reactor is carried out, is in the range from 10 to 100 bar, more preferably from 10 to 80 bar, more preferably from 10 to 60 bar, more preferably from 10 to 40 bar, and still more preferably from 10 to 20 bar.

According to the desired amount of oxygen to be removed from (GII) in stage (III) of the inventive process, it may be necessary to feed the product stream leaving the second reactor of the cascade into at least one further reactor. Preferably, the cascade comprises three or four serially coupled reactors, more preferably three serially coupled reactors.

Thus, the product stream leaving the second reactor is then fed to a third reactor of the cascade. Prior to being fed into the third reactor, the product stream is preferably brought to a temperature of from 100 to 300° C., more preferably from 150 to 300° C. and still more preferably from 150 to 250° C. If necessary, a stream comprising hydrogen, preferably a stream essentially consisting of hydrogen, is added to the product stream leaving the second reactor. Most preferably, the amount of hydrogen added is adjusted so that the molar ratio of hydrogen:oxygen is smaller than 5, preferably smaller than or equal to 4.5, more preferably smaller than or equal to 4.0, more preferably smaller than or equal to 3.5, more preferably smaller than or equal to 3. Still more preferably, the molar hydrogen:oxygen ratio is in the range from 0.1:1 to 4.5:1, more preferably from 0.2:1 to 4.0:1, more preferably from 0.3:1 to 3.5:1, more preferably from 0.4:1 to 3.0:1, more preferably from 0.5:1 to 3.0:1, more preferably from 0.6:1 to 2.0:1 and still more preferably from 0.7:1 to 1.5:1. Thus, if the product stream leaving the second reactor comprises an amount of hydrogen in the preferred ranges, it is not necessary to add an additional stream comprising hydrogen.

The pressure and temperature of the reaction in the third reactor are preferably adjusted so that the adiabatic temperature increase in the second reactor does not exceed 100° C., preferably 90° C., more preferably 80° C. and still more preferably 70° C. Most preferably, the pressure at which the reaction in the third reactor is carried out, is in the range from 10 to 100 bar, more preferably from 10 to 80 bar, more preferably from 10 to 60 bar, more preferably from 10 to 40 bar, and still more preferably from 20 to 40 bar.

According to a preferred alternative, mixture (GII) is fed into a single reactor, more preferably a single tube reactor, more preferably a single multi-tube reactor and more preferably a single fixed-bed multi-tube reactor. Still more preferably, the single fixed-bed multi-tube reactor is equipped with suitable cooling means so as to remove at least partially the heat resulting from the reaction in the reactor. More preferably at least 65% of the reaction heat is removed. Still more preferably, from 65 to 95%, more preferably from 70 to 90% and still more preferably from 75 to 85% of the reaction heat are removed. Thus, it was surprisingly found that it is sufficient to remove only a portion of the reaction heat, most preferably from 75 to 85% of the reaction heat. All suitable cooling agents can be employed. Especially preferred are oils, alcohols, liquid salts or water, such as river water, brackish water and/or sea water, which can in each case, for example, preferably be taken from a river and/or lake and/or sea close to the chemical plant in which the reactor of the invention and the process of the invention are used and, after any necessary suitable removal of suspended material by filtration and/or sedimentation, be used directly without further treatment for cooling purposes, with oils being especially preferred.

In case above-mentioned single reactor is used, molar hydrogen:oxygen ratios in the feed are preferred which are preferably in the range of from 1.5:1 to 4.0:1, more preferably from 2.0:1 to 4.0:1, more preferably from 2.0:1 to 3.5:1 and still more preferably from 2.5:1 to 3.5:1.

In case above-mentioned single reactor is used, no reactor cascade and no intermediate cooling is necessary. Surprisingly, it was found that effective removal of oxygen can be achieved using a single reactor, most preferably a multi-tube fixed-bed reactor, at low molar hydrogen:oxygen ratios, most preferably from 2.5:1 to 3.5:1, whereby only a portion of the reaction heat, most preferably from 75 to 85%, has to be removed at comparatively low temperatures, most preferably from 200 to 300° C., and comparatively low pressures, most preferably from 10 to 20 bar.

Generally, it is possible to use two or more reactors in parallel. At least two reactors in parallel most preferably allow for a continuous process if the catalyst in a first reactor has been deactivated to an undesired extent. In this case, reaction is stopped in this reactor and continued in at least one second reactor of the parallel reactors in which the reaction is performed in the same manner as in the first reactor. In the meantime, the deactivated catalyst of the first reactor is suitably regenerated inside or outside the first reactor.

This possibility of using at least one reactor which is connected in parallel with a given reactor can be also applied to each reactor of the other above-described alternatives. As to above-described reactor cascade, for example, at least one of the reactors coupled in series can have at least one parallel counterpart.

Therefore, according to this embodiment of the present invention wherein a single reactor, more preferably a single tube reactor, more preferably a single fixed-bed tube reactor and more preferably a single fixed-bed multi-tube (or tube bundle) reactor is employed, the mixture (GII) leaving stage (II) of the inventive process is heated to a temperature of from 100 to 300° C., more preferably from 150 to 300° C. and still more preferably from 150 to 250° C. Prior to being fed into the said first reactor, a stream comprising hydrogen, preferably a stream essentially consisting of hydrogen, is added to (GII). Further, such tube bundle reactors are preferably shell-and-tube reactors comprising a multitude of tubes such as from 5 to 100, preferably from 100 to 800, more preferably from 400 to 600 tubes, and additionally comprising said shell which is preferably e thermo jacket. Preferably, at least one suitable heat transfer medium is passed through the shell- and tube reactor, preferably through the thermo jacket, thus allowing for adjusting the temperature within the tubes to one or more desired values, either by heating, such as heating the tubes containing the catalyst before the reaction mixture is passed through the tubes, or by cooling, such as cooling when the reaction mixture flows through the tubes and reaction occurs. Most preferably, a shell-and-tube reactor used according to the present invention is installed such that the tubes are in an upright position. Generally, it is possible to pass the reaction mixture in upflow mode or in downflow mode through the tubes. Most preferably, the reaction mixture is passed through the tubes in downflow mode. Typically, such hydrogenation reaction wherein tube bundle reactors are used are conducted in continuous mode.

Therefore, the present invention also relates to the process as described hereinabove wherein the reaction in stage (III) is a continuous reaction, and wherein the reaction is carried out in at least one, preferably exactly one tube bundle reactor comprising from 400 to 600 tubes and a thermo jacket, and wherein the at least one reactor is operated in downflow mode.

It was surprisingly found that the presence of methanol, preferably in small amounts, being a system intrinsic compound, enhances the conversion of oxygen by formation of carbon dioxide. Thus, the product stream leaving the last reactor of the cascade, preferably the fourth or third or second reactor, more preferably the fourth or third reactor, still more preferably the third reactor, or leaving the single reactor, has an oxygen content of at most 800 ppm, such as 500 ppm, at most 400 ppm, at most 300 ppm, or at most 200 ppm.

The product stream leaving the last reactor of the cascade or the single reactor may additionally comprise water. If present, water is preferably comprised in an amount of at most 10 wt.-%, preferably at most 7 wt.-% and still more preferably at most 5 wt.-%, based in each case on the weight of the product stream. In this case, it is preferred that the product stream leaving the last reactor of the cascade or the single reactor is subjected to cooling so that at least a portion of the water is condensed and thus separated from the product stream. After condensation of at least a portion of the water, the stream has a preferred water content of at most 0.5 wt.-%, more preferably of at most 0.4 wt.-%.

The optionally cooled product stream, from which water may have been separated, is then obtained as mixture (GIII) in the inventive process.

Therefore, the present invention also relates to a process as described above, wherein the mixture (GIII) resulting from (III) has an oxygen content of not more than 800 ppm. According to another preferred embodiment, (GIII) has an oxygen content of at most 150 ppm.

It was surprisingly found that, as far as the specific compositions are concerned which result from propene epoxidation reactions and which are subjected to stage (III) of the process according to the invention, the use of the specific catalyst allows for stable reaction in stage (III) for a period of at least 100 h, preferably at least 150 h, and still more preferably at least 200 h. The term "stable" as used in this context refers to a continuous process wherein the oxygen content of the mixture (GIII) obtained from (III) is not above the preferred value of 800 ppm or 150 ppm over the whole period.

Also, it was surprisingly found that the energy comprised in the effluent, i.e. the product stream obtained from the last reactor of the cascade, preferably the second, the third, or the fourth reactor, more preferably the third or fourth reactor and still more preferably the third reactor, or the product stream obtained from the single reactor, can be effectively used to bring the mixture (GII) at least partially to the desired temperature of from 100 to 300° C., more preferably from 150 to 300° C. and still more preferably from 150 to 250° C., prior to the feeding into the first reactor.

Therefore, the present invention also provides an efficient heat integrated method in which the product stream obtained from (III) is effectively used for bringing the feed stream of (III) to a preferred temperature useful for conducting the reaction in (III).

Thus, the present invention also relates to a process as described above, wherein the mixture leaving the last of the serially coupled reactors is at least partially used to at least partially heat the mixture (GII) to a temperature in the range of from 150 to 250° C.

Accordingly, the present invention also relates to a process as described above, wherein the mixture leaving the single reactor is at least partially used to at least partially heat the mixture (GII) to a temperature in the range of from 150 to 250° C.

In case the process of the present invention is started, the mixture (GII) can be heated to the preferred temperature by a support heat exchanger, e.g. an electrical heat exchanger, which is no longer necessary once the most preferably continuously conducted process is running and a heat exchanger used for bringing (GII) to the preferred temperature is driven by the product stream obtained from (III).

Therefore, according to a preferred embodiment of the present invention, the liquid or gaseous, more preferably gaseous mixture (GIII) obtained from (III) comprises of from 70 to 95 wt.-%, more preferably of from 75 to 95 wt.-% and still more preferably of from 85 to 95 wt.-% of propene, of from 1 to 20 wt.-%, more preferably of from 2 to 15 wt.-% and still more preferably of from 5 to 15 wt.-% of propane, and of at most 800 ppm, such as at most 400 ppm, or at most 300 ppm, or at most 200 ppm, or at most 150 ppm of oxygen.

The catalyst load in stage (III) is preferably in the range of from 10 to 1,000 g($O_2$)/(kg(catalyst)*h), more preferably of from 50 to 750 g($O_2$)/(kg(catalyst)*h) and still more preferably of from 50 to 500 g($O_2$)/(kg(catalyst)*h).

In case the catalyst used for the reaction in stage (III) is deactivated, it can be replaced by freshly prepared catalyst. Preferably, deactivated catalyst is suitably regenerated. Moreover, it is possible to regenerate a portion of the deactivated catalyst and replace the remaining portion by freshly prepared catalyst. If the reaction of stage (III) is carried out continuously, which is preferred, the reaction is stopped in the reactor once the catalyst is deactivated and without or essentially without interruption continued in at least one parallel reactor. If the catalyst is used in suspension mode, the deactivated catalyst is suitably separated and suitably regenerated. If the catalyst is used in fixed-bed mode, it can be suitably separated and regenerated outside the reactor in a suitable apparatus. While all suitable regeneration techniques are possible to reactivate a deactivated catalyst to a desired extent, preferably to such an extent that its performance is nearly or completely restored compared to freshly prepared catalyst, the following regeneration process is employed which comprises at least one of the following stages, most preferably all of the following stages (aa) to (cc), and which essentially consists of all of the following stages (aa) to (cc).

(aa) Purging the reactor or the apparatus which contains the deactivated catalyst with a suitable inert gas, preferably nitrogen, for a time sufficient to remove propene essentially completely from the reactor, preferably for a time in the range of from 0.1 to 48 h, more preferably of from 1 to 10 h and more preferably of from 1 to 5 h. At the beginning of purging the reactor, the reactor can have the temperature at which the reaction had taken place therein. Alternatively, the reactor can be cooled or heated to a desired temperature prior to purging.

(bb) Treating the catalyst with a gas mixture comprising oxygen, more preferably with a gas mixture essentially consisting of oxygen and at least one inert gas such as nitrogen and/or carbon dioxide. Preferably, the oxygen content of the gas mixture is from 0.1 to 30 vol.-%. Preferably, treatment with the gas mixture comprising oxygen is carried out for a time in the range of from 0.2 to 72 h, more preferably from 1.3 to 60 h, more preferably from 2.4 to 52 h. It is still more preferred to (aaa) first treat the deactivated catalyst with a gas mixture essentially consisting of oxygen and at least one inert gas for a time of from 0.1 to 24 h, more preferably of from 0.3 to 20 h, more preferably of from 0.4 to 16 h and still more preferably from 0.5 to 12 h, wherein the oxygen content of the gas mixture is preferably in the range of from 0.1 to 5, more preferably of from 0.3 to 5 and still more preferably in the range of from 0.5 to 5 vol.-% such as about 0.5, 1, 2, 3, 4, or 5 vol.-%, and (bbb) treat the such treated catalyst with a gas mixture essentially consisting of oxygen and at least one inert gas for a time of from 0.1 to 48 h, more preferably of from 1 to 40 h and more preferably of from 2 to 36 h, wherein the oxygen content of the gas mixture is higher compared the content of the gas mixture used in (aaa), wherein this content is preferably in the range of from more than 5 to 30, more preferably of from 6 to 30, more preferably from 10 to 30 and still more preferably in the range of from 10 to 25 vol.-% such as about 10, 15, 17.5, 20, 22.5 or 25 vol.-%.

(cc) Purging the reactor with an inert gas or a mixture of at least two inert gases. A preferred inert gas is nitrogen. Stage (cc) is most preferably carried out after stage (bb) to remove at least a portion, more preferably essentially all oxygen from the reactor.

In case the temperature in a given regeneration stage and/or between two regeneration stages has to be changed, the temperature can be increased or decreased continuously or step-wise or continuously and step-wise wherein the respective temperature ramps can be suitably chosen. Generally, temperature ramps of from 0.01 to 20° C./min are used.

If at least two of above-described regeneration stages are performed, it is preferred that they are performed in the given order.

Still more preferably, the regeneration process comprises at least (aa) wherein, even more preferred, the purging gas essentially consists of nitrogen.

Still more preferably, the regeneration process comprises at least (aa) wherein the purging gas essentially consists of nitrogen, (bb) wherein even more preferred, (aaa) and (bbb) are performed and wherein in (aaa) a gas mixture essentially consisting of oxygen and at least one inert gas with an oxygen content of 2 to 5 vol.-% and in (bbb) a gas mixture essentially consisting of oxygen and at least one inert gas with an oxygen content of more than 5 to 20 vol.-% are employed.

Still more preferably, the regeneration process essentially consists of (aa) wherein the purging gas essentially consists of nitrogen, (bb) wherein even more preferred, (aaa) and (bbb) are performed and wherein in (aaa) a gas mixture essentially consisting of oxygen and at least one inert gas with an oxygen content of 2 to 5 vol.-% and in (bbb) a gas mixture essentially consisting of oxygen and at least one inert gas with an oxygen content of more than 5 to 20 vol.-% are employed, (cc) wherein the purging gas essentially consists of nitrogen, and (dd) wherein, even more preferred, the reducing gas essentially consists of hydrogen.

It was surprisingly found that in stage (III) of the inventive process, only a very small amount of carbon dioxide is formed. Thus, the mixtures obtained from stage (III) preferably comprise at most 2.0 wt.-%, more preferably at most 1.9 wt.-% and still more preferably at most 1.8 wt.-% of carbon dioxide in case mixture (GII) fed into stage (II) comprises about 0.1 wt.-% of carbon dioxide.

Additionally, it was found that, for example, stage (III) of the present inventive process can be also applied for a process where oxygen has to be effectively removed from gas mixtures comprising at least one olefin which is different from propene and oxygen. Such gas mixtures may be, for example, mixtures comprising ethene and oxygen and result from epoxidation processes of ethene with oxygen or an oxygen delivering compound. Therefore, the present invention also relates to a process for removing oxygen from a gas mixture comprising oxygen and an olefin, preferably ethene, by subjecting this mixture to a work-up stage wherein the oxygen comprised in this mixture is at least partially reduced by reaction with hydrogen in the presence of a catalyst comprising copper in elemental and/or oxidic form and optionally at least one promoter chosen from the above mentioned group, supported on a suitable support, preferably on magnesium silicate. The amounts of copper and at least one promoter are described above. If necessary, also other stages of the process of the present invention can be applied or be adapted to these gas mixtures.

Stage (IV)

The mixture (GIII) obtained from stage (III) of the inventive process can be further worked up and/or used as feed stream for a suitable chemical process. Preferably, (GIII) is worked up, wherein even more preferably, propene is separated from (GIII). The separated propene can be used, e.g., as feed stream for a suitable process. More preferably, the propene separated from (GIII) is re-introduced as feed stream into stage (I) of the inventive process.

Therefore, the present invention also relates to a process as described above, the process additionally comprising (IV) separating propene from mixture (GIII) resulting from (III) and re-introducing the separated propene into (I).

Separation in (IV) can be performed according to any suitable method. Preferably, propene is separated in (IV) from (GIII) by distillation using at least one distillation column. Most preferably, one distillation column is used.

Distillation in (IV) is preferably carried out at a pressure in the range of from 16 to 35 bar, more preferably from 20 to 35 bar and still more preferably from 20 to 30 bar, the pressure being measured at the top of the column, using a distillation column preferably having of from 20 to 200, more preferably from 50 to 150 and still more preferably from 70 to 120 theoretical stages. Propene is most preferably obtained at a side offtake of the column.

The propene stream obtained from (IV), most preferably from the distillation column used in (IV), comprises at least 95 wt.-%, more preferably at least 96 wt.-% propene, based on the total weight of the stream. Additionally, the propene stream obtained from (IV) may comprise up to 5 wt.-%, preferably up to 4 wt.-% propane. In case (GIII) contains water and optionally methanol, this compounds are comprised in the propene stream obtained from (IV) in amounts well below 1 wt.-%.

Most preferably, the propene stream obtained from (IV) comprises at most 50 ppm, more preferably at most 40 ppm, more preferably at most 30 ppm, more preferably at most 20 ppm and still more preferably at most 10 ppm of oxygen. Yet more preferably, no traces of oxygen can be detected in the propene stream separated from (GIII). Since this propene stream is preferably recycled as feed stream into stage (I) of the inventive process, the present invention provides an integrated process in which propene is recycled and, simultaneously, the oxygen concentration of the reaction mixture in (I) is effectively prevented from increasing by substantially removing oxygen from the propene recycling stream.

Together with the heat integration method described above with regard to stage (III), the present invention thus provides a highly integrated process, in terms of heat integration as well as in terms of compound recycling.

According to a preferred embodiment of the present invention, a process for producing propylene oxide is provided, the process comprising (I) reacting propene with hydrogen peroxide in the presence of a catalyst to give a mixture (GI) comprising of from 8 to 13 wt.-% of propylene oxide, of from 2 to 7 wt.-% of unreacted propene, of from 0.01 to 1 wt.-% of propane, and of from 0.02 to 0.5 wt.-% of oxygen;

(II) separating propylene oxide from mixture (GI) to give a mixture (GII), optionally after an intermediate stage, comprising of from 85 to 90 wt.-% of propene, of from 5 to 10 wt.-% of propane, and of from 3 to 5 wt.-% of oxygen, in each case based on the total weight of the mixture (GII);

(III) reducing the oxygen comprised in mixture (GII) at least partially by addition of and reaction with hydrogen to mixture (GII) in the presence of a catalyst comprising copper in elemental and/or oxidic form and at least one promoter supported on magnesium silicate, the catalyst having a BET surface determined according to DIN 66131 of 20 to 300 m$^2$/g, and a content of copper form 40 to 50 wt.-%, based on the total catalyst weight, mixture (GIII) having a preferred oxygen content of 800 ppm at most;

(IV) separating propene from mixture (GIII) resulting from (III) and re-introducing the separated propene, having a preferred oxygen content of 10 ppm at most, into (I), wherein in (III), the reduction reaction is performed at a temperature of preferably 175 to 250° C. and at a pressure in the range of from 10 to 20 bar, and wherein in (III), the hydrogen is added in an amount so that the molar ratio of hydrogen to oxygen is in the range of from 0.3:1 to 3.5:1.

While not preferred, also mixtures comprising propene and oxygen may be introduced into the inventive stage (III) of the present process, which mixtures are obtained from a process for the epoxidation of propene which comprises at least one of the following stages:

(a) Propene is reacted with hydrogen peroxide in a fixed-bed tube-bundle reactor. As catalyst, preferably a TS-1 catalyst is employed, and methanol is preferably used as solvent. The hydrogen peroxide solution is preferably an aqueous solution and obtained from an anthrachinone process and has a concentration of about 40 wt.-% with respect to hydrogen peroxide. Prior to use, the hydrogen peroxide solution can be adjusted to a pH of about 4.5 with, e.g., ammonia. Preferably, the reactor is configured for downflow mode. The reaction mixture may be present as two liquid phases, one of which is rich in propylene, the other being rich in water. Moreover, the reactor can be operated such that the catalyst is maintained in trickle-bed state.

(b) After leaving the reactor, the reaction mixture is fed into a flash tower or pre-evaporator. Preferably, the pre-evaporator has a maximum of 5 theoretical stages. The pre-evaporator may be configured so that at least 99% of the propylene oxide comprised in the feed obtained from (a) goes overhead and at least 99% of the water comprised in the feed obtained from (a) leaves the pre-evaporator through the bottoms.

(c) Then gaseous product obtained from the top in (b) is fed to a partial condenser. The condensed product comprises, e.g., propylene oxide, methanol and optionally propene. The gaseous product comprises propene and optionally small amounts of propane and/or oxygen and/or propylene oxide. The gaseous stream may be washed with methanol, e.g. in counter-current mode. The stream comprising propene, oxygen and propane can be fed as feed stream into stage (III) of the inventive process.

(d) The stream obtained from (c), comprising propene, propane and oxygen can be subjected to a suitable treatment such as an absorption treatment where propene and propane are absorbed in a suitable absorption agent such as methanol. The remaining oxygen may be diluted with a suitable gas such as an inert gas. Dissorbed propene, comprising oxygen and optionally propane, can be fed as feed stream into stage (III) of the inventive process.

(e) The bottoms product obtained from (b), comprising, e.g., water, unreacted hydrogen peroxide and optionally other high boilers is fed to a hydrogenation stage.

Generally, the present invention also describes the use of a supported copper catalyst, generally and as far as preferred embodiments are concerned as defined above, for reducing oxygen comprised in gas mixtures, preferably in gas mixtures obtained from epoxidation reaction, in particular from gas mixtures obtained from epoxidation from propene.

DETAILED DESCRIPTION OF THE FIGURES

FIG. 1: shows a heat exchanger which can be used for the reaction in (III). Through (1), mixture (GII) is fed into the heat exchanger, through (2), the product stream is obtained. Air (3) is pressed into the apparatus, which is horizontally configured. The curved arrow denotes the rotation direction of the propeller (M). The tubes through which the feed is passed, contain the catalyst.

Figure 2:
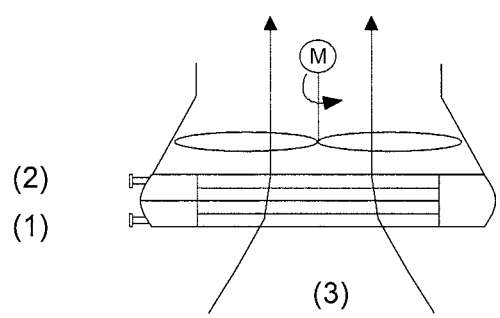

FIG. 2: shows a heat exchanger which can be used for the reaction in (III). Through (1), mixture (GII) is fed into the heat exchanger, through (2), the product stream is obtained. Air (3) is drawn into the apparatus, which is horizontally configured. The curved arrow denotes the rotation direction of the propeller (M). The tubes through which the feed is passed, contain the catalyst.

Figure 3:
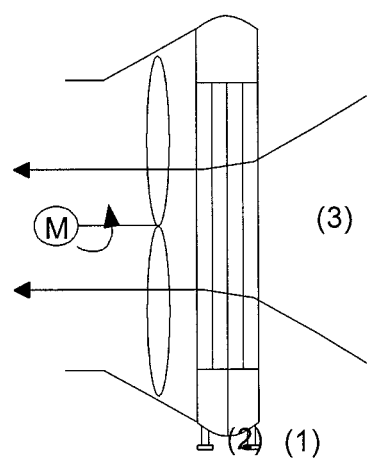

FIG. 3: shows a heat exchanger which can be used for the reaction in (III). Through (1), mixture (GII) is fed into the heat exchanger, through (2), the product stream is obtained. Air (3) is drawn into the apparatus, which is vertically configured. The curved arrow denotes the rotation direction of the propeller (M). The tubes through which the feed is passed, contain the catalyst.

Figure 4:
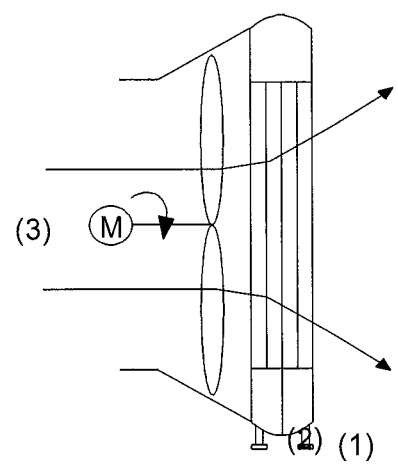

FIG. 4: shows a heat exchanger which can be used for the reaction in (III). Through (1), mixture (GII) is fed into the heat exchanger, through (2), the product stream is obtained. Air (3) is pressed into the apparatus, which is vertically configured. The curved arrow denotes the rotation direction of the propeller (M). The tubes through which the feed is passed, contain the catalyst.

FIG. 5: shows an adiabatic fixed-bed shaft reactor with back-mixing without direct cooling of the reaction mixture which can be used for the reaction in (III). Mixture (GII) is fed as feed stream (1) into the reactor (2) wherefrom the product stream (3) is obtained. A portion (4) is separated from (3) to obtain a portion (5) which is cooled in a heat exchanger (6) and subsequently mixed back with the feed stream (1).

Figure 6:
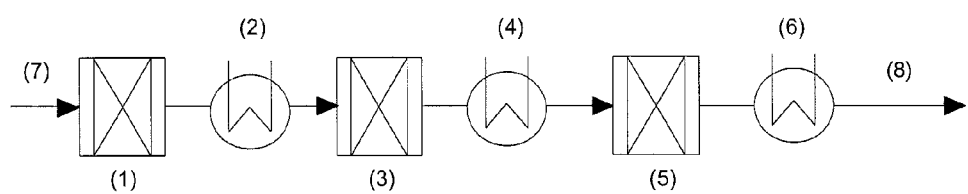

FIG. 6: shows a cascade of three serially coupled adiabatic fixed-bed shaft reactors (1), (3) and (5) with heat exchangers (2) and (4) for intermediate cooling and a heat exchanger (6) for final cooling. Into the first reactor (1), (GII) is fed as feed stream (7). From the heat exchanger used for the final cooling, the product stream (8) is obtained.

FIG. 7: shows an adiabatic fixed-bed reactor (R) in which an oxygen containing stream (O) is introduced. Before stream (O) is fed into the reactor, hydrogen (H) is admixed. The reactor effluent (P) which is essentially free of oxygen is used to heat stream (O) in heat exchanger (E). When starting the reaction in (R) in a continuos process, no effluent is available to heat stream (O). For this purpose, (O) is electrically heated in electric heat exchanger (C).

Figure 8:
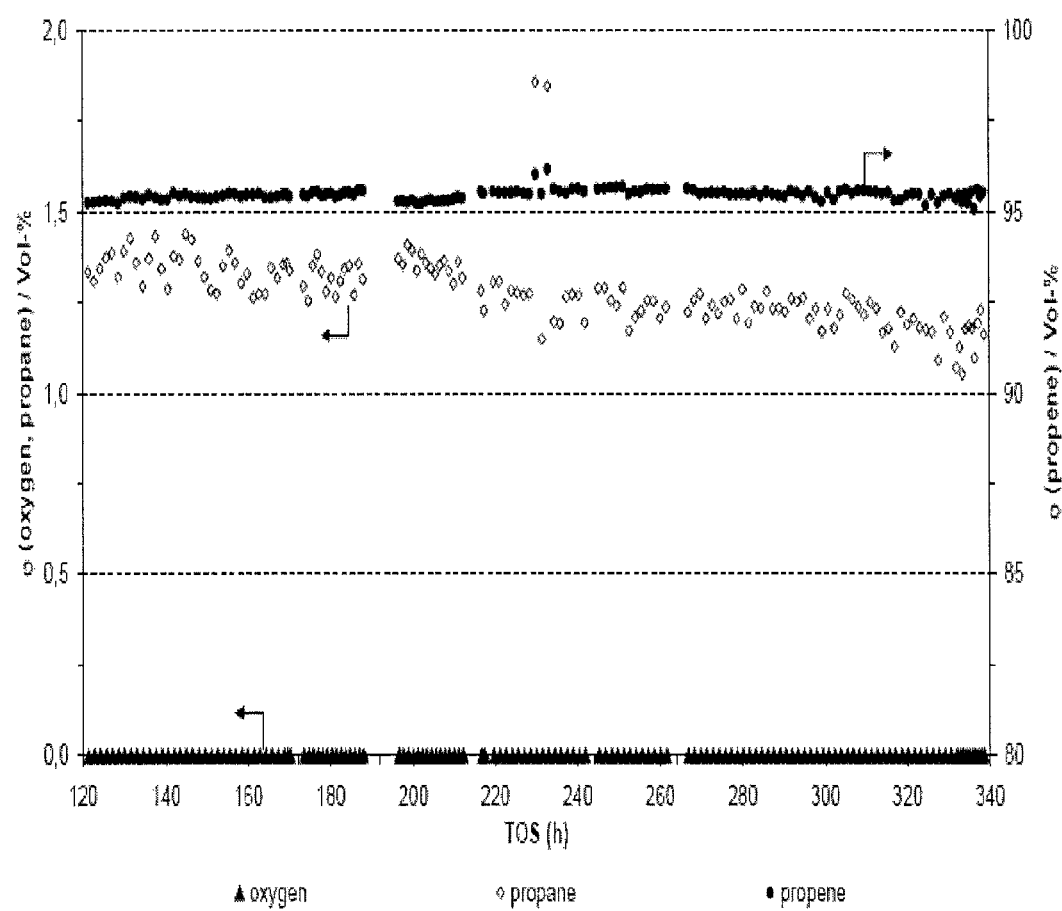

FIG. 8: shows the volume fractions of propene, propane, oxygen, measured at the reactor outlet, in dependence of the runtime as result of an experiment according to example 2 for reducing oxygen comprised in the mixture GII by reaction with hydrogen. In FIG. 8, the symbols ▲ ◊ ● stand for the concentration of components oxygen, propane and propene expressed in vol.-% in the reactor output stream as measured by gas chromatography and TOS stands for "Time On Stream", measured after the start-up with a fresh catalyst.

The inventive process is illustrated by the following examples.

EXAMPLES

Epoxidation of Propene (Examplary)

A stream consisting of 54.5 g/h chemical grade propylene (96 wt.-%) was epoxidized with 74.7 g/h crude aqueous hydrogen peroxide (40 wt.-%) in the presence of a methanol stream (299 g/h) at a pressure of 20 bar. Epoxidation was carried out in the presence of 100 g TS-1 catalyst. The yield of propylene oxide, based in hydrogen peroxide, was 93.2% at a hydrogen peroxide conversions of 99.8%. The TS-1 catalyst was in the form of strands having a mean diameter of about 1.5 mm, and a mean length of about 5 mm, the strands consisting of titanium silicalite-1 as catalytically active material (about 75 wt.-%) contained in a mesoporous amorphous silica matrix (about 25 wt.-%). Epoxidation was carried out in isothermal fixed bed mode at a mean bed temperature of about 50° C.

Separation of the light components, methanol and water from the main reaction product was performed in a distillation tower having 40 trays. At a top pressure of 1.1 bar, a top stream of the distillation tower was obtained giving a stream (17.5 g/h) containing 83 wt.-% propene, 12 wt.-% propane, 0.6 wt.-% oxygen, 3.3 wt.-% methanol, and 1 wt.-% water. Propylene oxide, methanol and water were taken from the bottom of the distillation tower.

Preparation of a Copper Catalyst

A copper catalyst was prepared according to the example of EP 0 427 062 A2, catalyst 2, page 4, lines 41 to 50.

Hydrogenation (1$^{st}$ Example; Non-industrial Size Design)

The equipment used comprises mass flow controllers for dosing gases and HPLC pump for dosing liquids. The reduction of oxygen by conversion with hydrogen in the presence of propene, water and methanol is carried out continuously in the reaction tube with an inner diameter of 18 mm and a length of 600 mm. The fixed bed reactor is electrically heated. The temperature is controlled via thermocouples in the heating jacket. The reactor is filled with 33 g of above-mentioned copper catalyst in the form of 3 mm*5 mm tablets. The remaining volume is filled up with inert material (steatite spheres with a diameter of 1.5 to 2.5 mm) above and below the catalyst in equal parts. Thus, the catalyst bed is centred in the reaction tube. The pressure is set to 15 bar via a regulating valve at the reactor exit. To avoid condensation, the tubes leading into and out of the reactor are heated (approximate temperature 100° C.). The gas stream entering the reactor and the reactor influent are analysed by gas chromatography.

As propene and oxygen containing stream, a stream was employed which contained 95.5 wt.-% propene, 0.6 wt.-% propane, 2.9 wt-% oxygen, 0.8 wt.-% methanol, and 0.2 wt.-% water, was subjected to hydrogenation. Such stream serves as an example for a stream which may essentially be obtained by carrying out an epoxidation reaction similar to the epoxidation as described above, followed, for example, by an intermediate stage as described in the context of the present invention wherein the oxygen content is increased.

By passing the inert section of the reactor, this stream (50 Nl/h) is preheated to the temperature of the heating jacket which is set to 215° C.

An oxygen conversion of at least 99.7% is achieved, corresponding to an oxygen content of the reactor effluent of 100 ppm. Hydrogen conversion was above 73%, propene conversion (due to hydrogenation to propane) was about 0.9%.

As shown in FIG. 8, the reaction is stable in the period of more than 200 hours, with excellent conversion values over the whole period.

After a total time on stream of 1250 hours the catalyst was removed and its crush strength was measured on a Z2.5 apparatus (Zwick Company) using a preliminary test force (also known as "preload", "minor load" or German "Vorkraft") of 0.5 N, a preliminary test force speed ("Vorkraft-Geschwindigkeit") of 10 mm/min and a test speed (German "Prüfgeschwindigkeit") of 1.6 mm/min. Tablets were taken both in the first half (entry side) and second (exit side) of the reactor and both showed a crush strength of 20 N (average of 10 single measurements). The BET surface of the used catalyst was found to be between 45 and 50 m²/g, compared to the BET surface of the freshly employed catalyst being 295 m² g.

Hydrogenation (2nd Example, Industrial-size Design)

The reduction of oxygen by conversion with hydrogen in the presence of propene, water and methanol was carried out continuously in a tube bundle reactor with 552 tubes. The tubes were 4 m long and had an inner diameter of 34 mm. The reactor was installed in an upright position, the reaction media was flowing inside the tubes in a downflow direction. The shellside of the reactor was cooled by a heat transfer medium. Before start of the reaction the reactor was heated up to a temperature of approximately 180° C. by the heat transfer medium. The temperature was controlled via multithermocouples in two of the reactor tubes, by thermocouples in the inlet and outlet of the reactor tube side and in the inlet and outlet of the reactor shell side. Each reaction tube was filled with 2.59 kg of the above-mentioned copper catalyst in the form of 3 mm×5 mm tablets, resulting in a reaction bed of 3.4 meter height. The remaining volume was filled up with inert material (steatite spheres with a diameter of 1.5 to 2.5 mm) at a height of 0.5 m above and 0.1 m below the catalyst bed. The pressure was set to 15.5 bar via a regulating valve at the reactor exit. The inlet temperature of the reactor was approx. 187° C., the outlet temperature was approx. 196° C. The temperature of the heat transfer media on the shell side was held at approx. 194° C.

A propene and oxygen containing gaseous stream of 11.6 t/h which was obtained by carrying out an epoxidation reaction similar to the epoxidation as described above, containing 92.6 wt.-% propene, 3.7 wt.-% propane, 0.3 wt.-% oxygen and 2.8 wt-% methanol was first subjected to a partial condensation at a pressure of 16.1 bar and a temperature of 37.3° C. After separation of the liquid phase a gaseous stream of 3.1 t/h was obtained, containing 92.9 wt.-% propene, 2.8 wt.-% propane, 1.4 wt-% oxygen and 1.0 wt-% methanol. Before entering the above described reactor, this stream was mixed with a stream of 11.6 kg/h hydrogen (technical grade, purity >99.5%) and a stream of 308 kg/h of water (as steam) in a static mixer.

An oxygen conversion of at least 90.2 was achieved, corresponding to an oxygen content of the reactor effluent of 800 ppm. Hydrogen conversion was at 28%, propene conversion (due to hydrogenation to propane) was below 1%.

We claim:

1. A process for producing propylene oxide, comprising
   (I) reacting propene with hydrogen peroxide in the presence of a zeolite as a first catalyst to obtain a mixture GI comprising propylene oxide, unreacted propene, and oxygen;
   (II) separating propylene oxide from the mixture GI to obtain a mixture GII comprising propene and oxygen;
   (III) adding hydrogen to the mixture GII and reducing the oxygen of mixture GII at least partially by reaction with hydrogen in the presence of a second catalyst comprising copper in elemental form, oxidic form, or both forms, on a support, wherein the copper is present on the support in an amount of 30 to 80 wt. % based on a total catalyst weight and calculated as CuO, to obtain a mixture GIII.

2. The process of claim 1, wherein the second catalyst comprises copper in an amount of 40 to 50 wt.-%, based on a total catalyst weight and calculated as CuO.

3. The process of claim 1, wherein the support of the second catalyst comprises an inorganic material comprising silicon, oxygen, and at least one element selected from the group consisting of an alkali metal and an alkaline earth metal.

4. The process of claim 1, wherein the support comprises at least 99 wt.-% of magnesium silicate, based on a total weight of the support.

5. The process of claim 1, wherein the second catalyst comprises no catalytically active metal other than copper.

6. The process of claim 1, wherein the second catalyst further comprises at least one promoter selected from the group consisting of Li, Na, K, Rb, Cs, Be, Ca, Sr, Ba, Sc, Ti, V, Nb, Cr, Mo, W, Mn, Fe, Co, Ni, and Zn.

7. The process of claim 1, wherein the first catalyst is a zeolite catalyst comprising titanium, and the reacting is performed in the presence of methanol as a solvent.

8. The process of claim 1, wherein the mixture GII further comprises propane.

9. The process of claim 8, wherein the mixture GII comprises 1.0 to 5 wt.-% of oxygen, 85 to 97.5 wt.-% of propene, and 0.5 to 10 wt.-% of propane, in each case based on a total weight of the mixture GII.

10. The process of claim 1, wherein in (III), hydrogen is added in an amount such that a molar ratio of hydrogen to oxygen is in a range of 0.1:1 to 4.5:1.

11. The process of claim 1, wherein in (III), the reducing is performed at a temperature of 100 to 500° C., and a pressure of 0.1 to 100 bar.

12. The process of claim 1, comprising at least partially heating the mixture GII to a temperature of 150 to 300° C. with heat from at least part of the mixture GIII.

13. The process of claim 1, wherein the mixture GIII comprises not more than 800 ppm of oxygen.

14. The process of claim 1, wherein at least stage (III) is performed continuously, with an operating time of at least 200 h.

15. The process of claim 1, further comprising
   (IV) separating propene from mixture GIII and re-introducing the separated propene into (I).

16. The process of claim 1, wherein, between stages (II) and (III), mixture GII is compressed from a pressure of 1 to 5 bar to a pressure of 15 to 20 bar.

17. The process of claim 1, comprising
   (I) reacting propene with hydrogen peroxide in the presence of a titanium silicalite catalyst, to obtain the mixture GI comprising 8 to 13 wt.-% of propylene oxide, 2 to 7 wt.-% of unreacted propene, 0.01 to 1 wt.-% of propane, and 0.02 to 0.5 wt.-% of oxygen;
   (II) separating propylene oxide from the mixture GI to give, optionally after at least one intermediate stage, a mixture GII comprising 85 to 97.5 wt.-% of propene, 0.5 to 10 wt.-% of propane, and 1.0 to 5 wt.-% of oxygen, in each case based on a total weight of the mixture GII;
   (III) adding hydrogen to the mixture GII and reducing the oxygen of mixture GII at least partially by reaction with hydrogen in the presence of the second catalyst comprising (i) copper in elemental form, oxidic form, or both forms, and (ii) at least one promoter supported on magnesium silicate, the catalyst having a BET surface determined according to DIN 66131 of 20 to 300 m²/g, and a copper content of 40 to 50 wt.-%, based on a total catalyst weight and calculated as CuO, to obtain a mixture GIII having an oxygen content of 800 ppm at most;
   (IV) separating propene from mixture GIII and re-introducing the separated propene into (I),
   wherein in (III), the reducing is performed at a temperature of 175 to 250° C., and at a pressure of 10 to 20 bar, and wherein in (III), the hydrogen is added in an amount such that a molar ratio of hydrogen to oxygen is in a range of 0.3:1 to 3.5:1.

18. The process of claim 1, wherein at least stage (III) is performed continuously, with an operating time of at least 1000 h.

19. The process of claim 17, wherein at least stage (III) is performed continuously, with an operating time of at least 1000 h.

20. The process of claim 17, wherein the titanium silicalite catalyst is a titanium silicalite-1 (TS-1) catalyst.

* * * * *